(12) United States Patent
Ishii

(10) Patent No.: US 8,824,629 B2
(45) Date of Patent: Sep. 2, 2014

(54) RADIATION IMAGING SYSTEM AND IMAGE PROCESSING METHOD

(71) Applicant: FUJIFILM Corporation, Tokyo (JP)

(72) Inventor: Hiroyasu Ishii, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 108 days.

(21) Appl. No.: 13/753,180

(22) Filed: Jan. 29, 2013

(65) Prior Publication Data

US 2013/0142308 A1 Jun. 6, 2013

Related U.S. Application Data

(63) Continuation of application No. PCT/JP2011/065572, filed on Jul. 7, 2011.

(30) Foreign Application Priority Data

Aug. 19, 2010 (JP) ................................ 2010-183839
Feb. 2, 2011 (JP) ................................ 2011-020503

(51) Int. Cl.
*G01N 23/04* (2006.01)
*A61B 6/00* (2006.01)

(52) U.S. Cl.
CPC .............. *G01N 23/04* (2013.01); *A61B 6/5264* (2013.01); *A61B 6/484* (2013.01); *A61B 6/488* (2013.01); *A61B 6/5235* (2013.01); *A61B 6/4291* (2013.01)
USPC ......................................... 378/62; 378/98.12

(58) Field of Classification Search
USPC ...................................... 378/2, 62, 98.12, 70
See application file for complete search history.

(56) References Cited

U.S. PATENT DOCUMENTS 5,812,629 A * 9/1998 Clauser ........................ 378/62

(Continued)

FOREIGN PATENT DOCUMENTS

| JP | 2001-153797 A | 6/2001 |
| JP | 2002-336230 | 11/2002 |

(Continued)

OTHER PUBLICATIONS

C. David et al., "Differential x-ray phase contrast imaging using a shearing interferometer"; Applied Physics Letters, Oct. 21, 2002; pp. 3287-3289; vol. 81, No. 17; American Institute of Physics.
Hector Canabal et al.; "Improved phase-shifting method for automatic processing of moire deflectograms"; Applied Optics, Sep. 10, 1998; pp. 6227-6233; vol. 37, No. 26; Optical Society of America.

*Primary Examiner* — Hoon Song
(74) *Attorney, Agent, or Firm* — Jean C. Edwards, Esq.; Edwards Neils PLLC

(57) ABSTRACT

In each of a first phase shift differential image produced in the absence of a subject in preliminary imaging and a second phase shift differential image produced in the presence of the subject in main imaging, boundaries, at each of which a value changes from $\pi/2$ to $-\pi/2$ or from $-\pi/2$ to $\pi/2$, are determined. First and second staircase data in each of which a value changes by $\pi$ or $-\pi$ when crossing each of the boundaries in a predetermined direction is produced. The first and second staircase data is added to the first and second phase shift differential images to produce first and second added phase shift differential image, respectively. The first added phase shift differential image is subtracted from the second added phase shift differential image to produce a corrected phase shift differential image.

10 Claims, 18 Drawing Sheets

(56) References Cited

U.S. PATENT DOCUMENTS

| | | |
|---|---|---|
| 7,180,979 B2 | 2/2007 | Momose |
| 2010/0290590 A1 | 11/2010 | Ouchi et al. |
| 2011/0235780 A1* | 9/2011 | Tada .............................. 378/62 |

FOREIGN PATENT DOCUMENTS

| | | |
|---|---|---|
| JP | 4445397 B2 | 1/2010 |
| WO | WO/2010/050483 A1 | 5/2010 |
| WO | WO/2010/050611 A1 | 5/2010 |

* cited by examiner

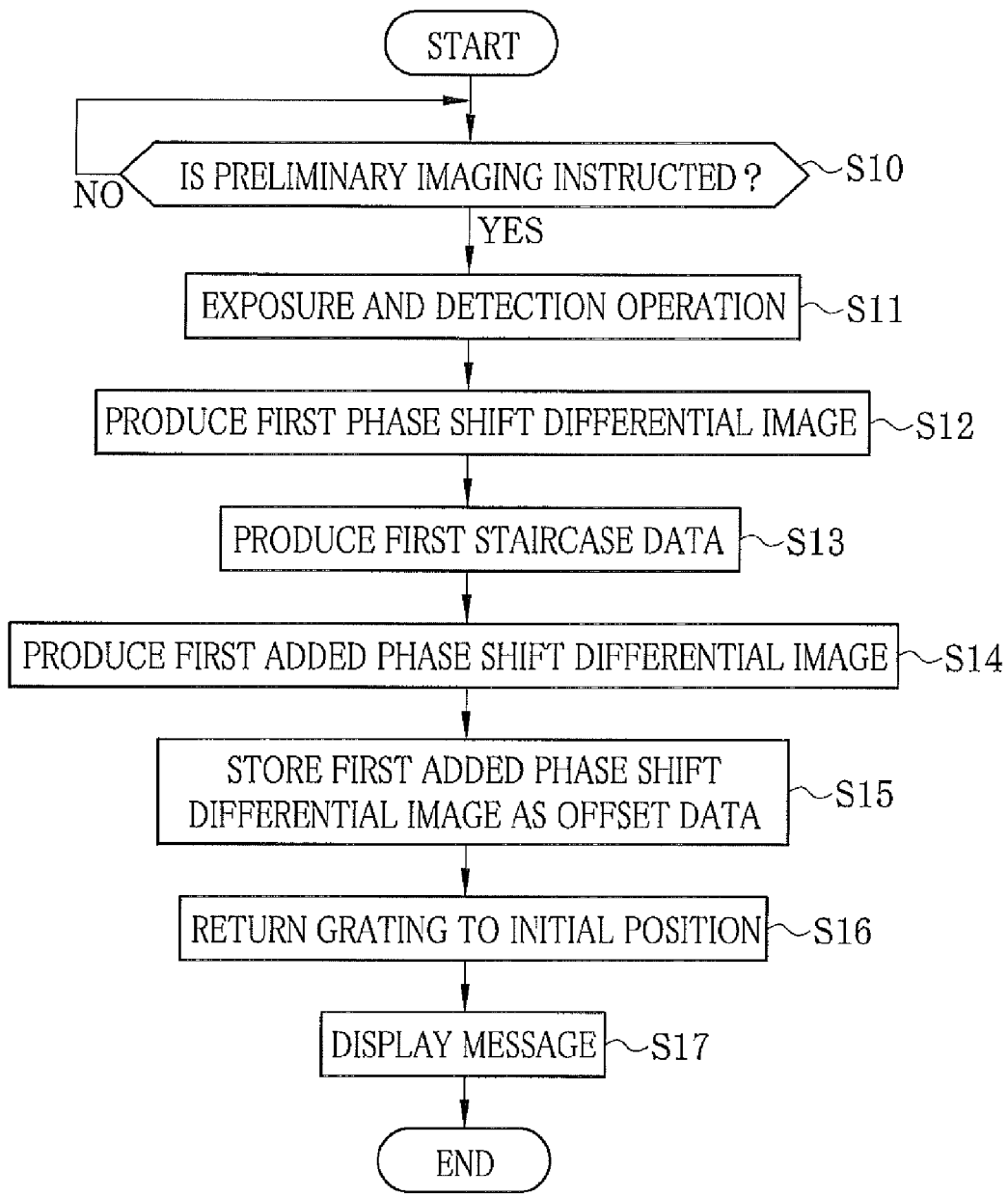

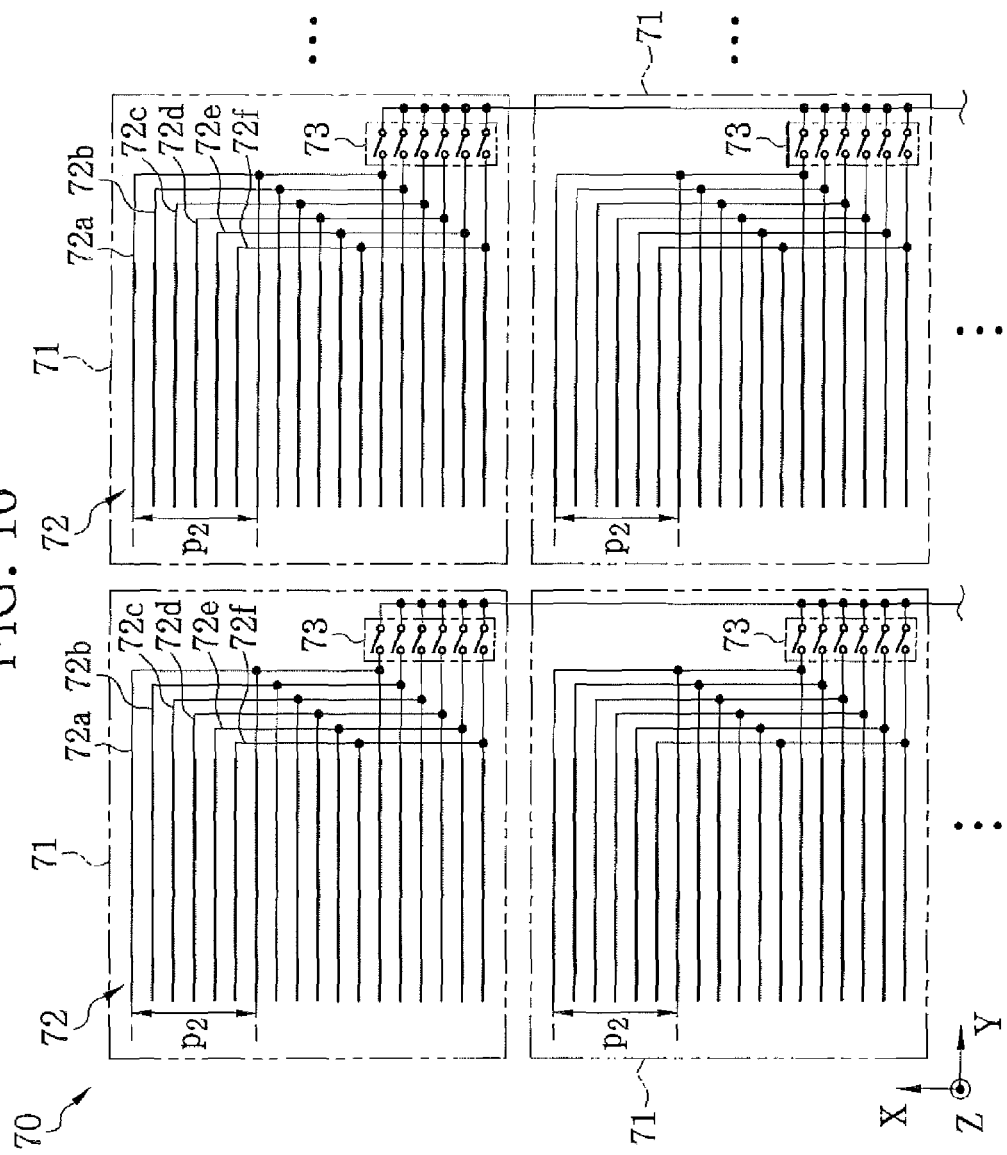

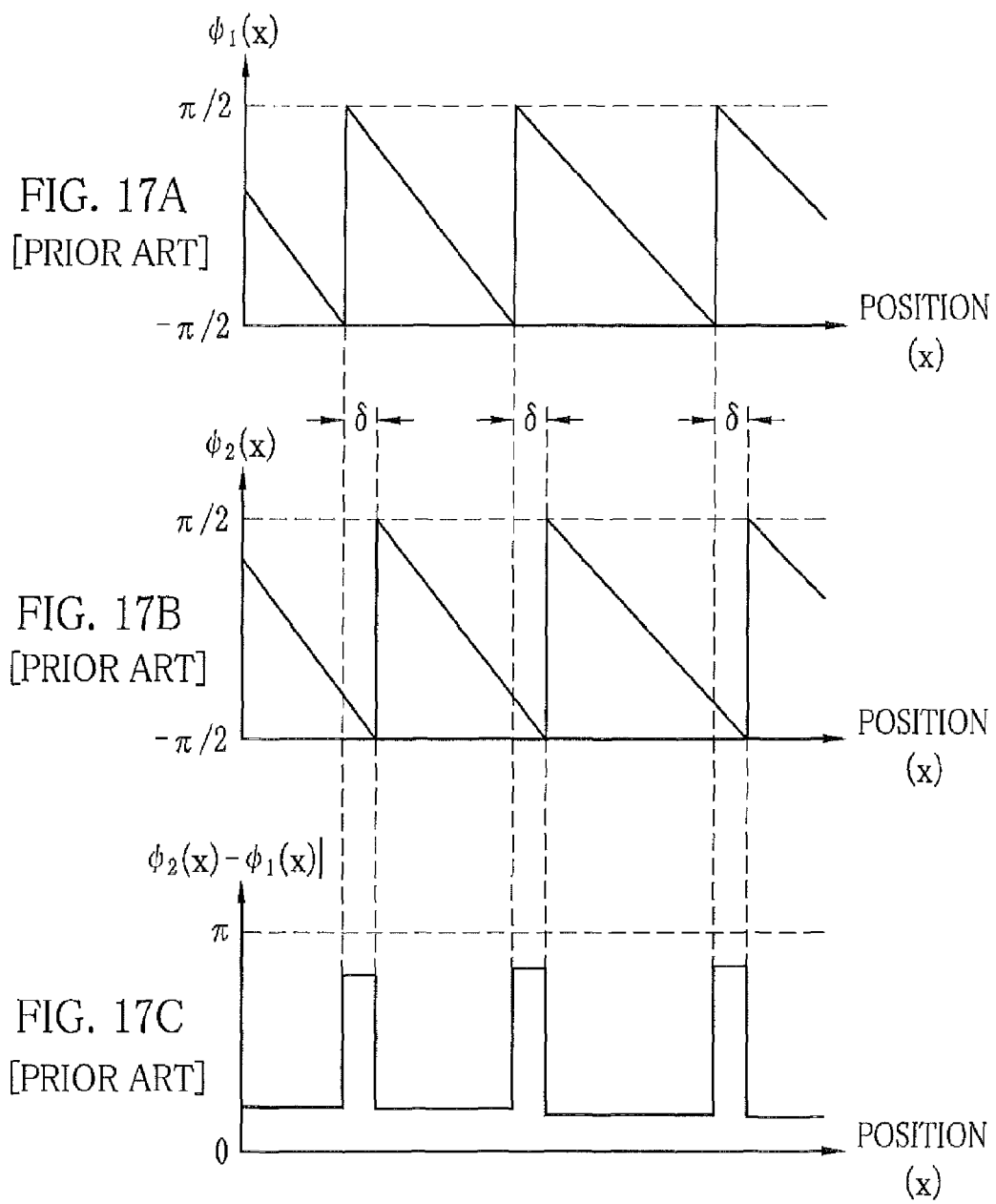

RADIATION IMAGING SYSTEM AND IMAGE PROCESSING METHOD

CROSS-REFERENCE TO RELATED APPLICATIONS AND PRIORITY CLAIMS

This application is a Continuation of International Application No. PCT/JP2011/065572 filed on Jul. 7, 2011, which was published under PCT Article 21(2) in Japanese, which is based upon and claims the benefit of priority from Japanese Patent Applications Nos. 2010-183839, which was filed Aug. 19, 2010, and 2011-020503, which was filed Feb. 2, 2011, the contents of all of which are incorporated herein by reference in their entirety.

BACKGROUND OF THE INVENTION

1. Field of the Invention

The present invention relates to a radiation imaging system using radiation to capture an image of a subject and an image processing method for a radiation imaging system, and particularly to a radiation imaging system using a fringe scanning method and an image processing method for a radiation imaging system using a fringe scanning method.

2. Description Related to the Prior Art

Radiation, for example, X-rays, is attenuated depending on an atomic number of an element constituting a substance, and density and thickness of a substance. By taking advantage of such properties, the X-rays are used as a probe for examining the inside of a subject in medical diagnoses and non-destructive inspections.

A common X-ray imaging system captures a transmission image of a subject disposed between an X-ray source that emits the X-rays and an X-ray image detector that detects the X-rays. The X-rays, emitted from the X-ray source toward the X-ray image detector, are attenuated (absorbed) by a substance, disposed on a path toward the X-ray image detector, by an amount corresponding to differences in properties (the atomic number, the density, and the thickness) of the elements in the substance. Then the X-rays are incident on each pixel of the X-ray image detector. Thus, the X-ray image detector detects and images an X-ray absorption image of the subject. Stimulable phosphor panels and flat panel detectors (FPDs) using semiconductor circuits are widely used as the X-ray image detectors.

The X-ray absorption performance of the substance decreases as the atomic number of the element constituting the substance decreases. This causes a problem that sufficient contrast cannot be obtained in the X-ray absorption image of living soft tissue or soft materials. For example, a cartilage portion constituting a joint of a human body and synovial fluid surrounding the cartilage portion are mainly composed of water, so that there is little difference between their amounts of X-ray absorption, resulting in little difference in contrast.

Due to such background, X-ray phase imaging has been actively studied recently. The X-ray phase imaging is used to obtain an image (hereafter referred to as the phase contrast image) based on phase shifts (angular changes), instead of intensity changes, of the X-rays caused by the subject. Generally, when the X-rays are incident on the subject, the subject interacts with the phase of the X-rays more strongly than with the intensity of the X-rays. Thus, the X-ray phase imaging using phase difference provides a high contrast image even if the subject has low X-ray absorption properties. An X-ray imaging system using an X-ray Talbot interferometer is known as one type of the X-ray phase imaging. The X-ray Talbot interferometer is composed of two transmission-type diffraction gratings and an X-ray image detector (see, for example, U.S. Pat. No. 7,180,979 corresponding to Japanese Patent No. 4445397 and C. David et al., Applied Physics Letters, Vol. 81, No. 17, October 2002, page 3287)

In the X-ray Talbot interferometer, the first diffraction grating is disposed behind the subject. The second diffraction grating is disposed downstream from the first diffraction grating by a Talbot length. The Talbot length is determined by a grating pitch of the first diffraction grating and an X-ray wavelength. The X-ray image detector is disposed behind the second diffraction grating. The Talbot length is a distance at which the X-rays passed through the first diffraction grating form a self-image (fringe image) due to Talbot effect. The self image is modulated by the phase shift of the X-rays caused by the subject disposed between the X-ray source and the first diffraction grating.

In the X-ray imaging system, the intensity of the fringe image is modulated by the superposition of the self image of the first diffraction grating onto the second diffraction grating. The phase contrast image of the subject is obtained from changes in the fringe image caused by the subject with the use of a fringe scanning method. In the fringe scanning method, the image is captured at each scan position with the second diffraction grating translationally moved (scanned) at a scanning pitch, being a fraction of the grating pitch, relative to the first diffraction grating in a direction substantially parallel with a plane of the first grating and substantially vertical to a direction of a grating line of the first diffraction grating. A phase shift differential image is produced from a phase shift value of an intensity modulation signal representing the intensity changes, relative to the respective scan positions, in pixel data of each pixel obtained with the X-ray image detector. The phase shift differential image corresponds to angular distribution of the X-rays refracted by the subject. The phase contrast image is produced by integrating the phase shift differential image in the direction of the scanning. The fringe scanning method is also employed in imaging apparatuses using laser (see, for example, Hector Canabal et al., Applied Optics, Vol. 37, No. 26, September 1998, page 6227).

In the fringe scanning method, the positional relationship between the first and second diffraction gratings strongly affects the image quality of the phase contrast image. Distortion, manufacturing error, arrangement error, or the like in the first or second diffraction grating results in offset, whose value corresponds to the distortion, the error, or the like, in the phase shift differential image. This deteriorates the image quality of the phase contrast image. In the U.S. Pat. No. 7,180,979, a phase shift differential image captured in the absence of a subject in preliminary imaging is stored as offset data. The offset data is subtracted from a phase shift differential image captured in the presence of the subject in main imaging. Thereby, the phase shift differential image produced reflects subject information only.

In the method for correcting the offset in the phase shift differential image disclosed in the U.S. Pat. No. 7,180,979, it is necessary that the preliminary imaging and the main imaging are performed under the same imaging conditions except for the presence and absence of the subject. When an initial position of the relative scanning of the first and second diffraction gratings in the main imaging is different from that in the preliminary imaging, artifact occurs due to the change in the initial position.

The artifact occurs due to an expression for calculating a phase shift value of an intensity modulation signal. As described in the U.S. Pat. No. 7,180,979, the phase shift value is calculated by extraction of argument in a complex plane, namely, an arctangent function ($\tan^{-1}$). The range is from $-\pi/2$ to $\pi/2$. As shown in FIG. 17A, when the phase shift differential image captured in the preliminary imaging contains moiré fringes due to the first and second diffraction gratings, a profile $\psi_1(x)$ with respect to the direction orthogonal to the moiré fringes is discontinuous across a portion (boundary) at which the value changes from $-\pi/2$ to $+\pi/2$ or from $+\pi/2$ to Hence, the profile $\psi_1(x)$ has a saw-like shape. The moiré fringes also appear in the phase shift differential image captured in the main imaging. As shown in FIG. 17B, a profile $\psi_2(x)$, in the direction orthogonal to the moiré fringes, has the saw-like shape in a similar manner.

When the initial position of the relative scanning of the first and second diffraction gratings in the main scanning is at the same position as that in the preliminary imaging, the profiles $\psi_1(x)$ and $\psi_2(x)$ have the same shape, so that they cancel out each other when subjected to the offset correction. When the initial position of the relative scanning in the main imaging is shifted from that in the preliminary imaging, there is a shift $\delta$ between the profiles $\psi_1(x)$ and $\psi_2(x)$. In this case, as shown in FIG. 17C, banding artifact with the value of approximately $\pi$ appears in a subtraction image produced by the offset correction of the profiles $\psi_1(x)$ and $\psi_2(x)$.

The artifact appears not only when there is a change in the initial scanning position between the preliminary and main imaging, but also when there is a change in the positional relationship of the first and second diffraction gratings between the preliminary and main imaging.

SUMMARY OF INVENTION

An object of the present invention is to provide a radiation imaging system for preventing artifact due to a change in position of a grating between preliminary and main imaging and an image processing method for a radiation imaging system.

To achieve the above objects, a radiation imaging system of the present invention is provided with a first grating, an intensity modulator, a radiation image detector, a phase shift differential image generator, a staircase data generator, a staircase data adder, and a subtraction processing section. The first grating passes radiation from a radiation source to form a first periodic pattern image. The intensity modulator provides intensity modulation to the first periodic pattern image to form at least one second periodic pattern image. The radiation image detector detects the second periodic pattern image to produce image data. The phase shift differential image generator produces a phase shift differential image based on the image data. The staircase data generator obtains one or more boundaries, at each of which a value changes from $\pi/2$ to $-\pi/2$ or from $-\pi/2$ to $\pi/2$, in each of a first phase shift differential image, produced by the phase shift differential image generator in absence of a subject in preliminary imaging, and a second phase shift differential image, produced by the phase shift differential image generator in presence of the subject in main imaging, and produces first staircase data and second staircase data each changing by $\pi$ or $-\pi$ when crossing the boundary in a predetermined direction. The staircase data adder adds the first staircase data to the first phase shift differential image to produce first added phase shift differential image. The staircase data adder adds the second staircase data to the second phase shift differential image to produce second added phase shift differential image. The subtraction processing section subtracts the first added phase shift differential image from the second added phase shift differential image to produce a corrected phase shift differential image.

It is preferable that the radiation imaging system further comprises a phase contrast image generator for integrating the corrected phase shift differential image in a direction of a period of the first grating to produce a phase contrast image.

It is preferable that the radiation imaging system further comprises storage for storing the first added phase shift differential image.

It is preferable that the radiation imaging system further comprises an input section and a controller. The input section inputs an instruction for the preliminary imaging or the main imaging. The controller controls the intensity modulator, the radiation image detector, the phase shift differential image generator, the staircase data generator, and the staircase data adder when the input section inputs the instruction for the preliminary imaging, and allows the storage to store the first added phase shift differential image produced by the staircase data adder.

It is preferable that the intensity modulator provides intensity modulation to the first periodic pattern image at relative positions out of phase with each other to produce the second periodic pattern images, and the radiation image detector detects the second periodic pattern images to produce the respective pieces of image data. The phase shift differential image generator calculates a phase shift value of an intensity modulation signal based on the pieces of image data to produce the phase shift differential image. The intensity modulation signal represents intensity changes in pixel data corresponding to the relative positions.

It is preferable that the intensity modulator is composed of a second grating and a scan mechanism, and a direction of a periodic pattern of the second grating is the same as that of the first periodic pattern image, and the scan mechanism moves one of the first and second gratings at a predetermined pitch.

It is preferable that the first grating is an absorption-type grating and projects the radiation from the radiation source as the first periodic pattern image onto the second grating.

It is preferable that the first grating is a phase-type grating and forms the radiation from the radiation source into the first periodic pattern image at a position of the second grating due to Talbot effect.

It is preferable that the radiation imaging system further comprises a source grating on an emission side of the radiation source.

An image processing method for a radiation imaging system provided with a first grating for passing radiation from a radiation source to form a first periodic pattern image, an intensity modulator for providing intensity modulation to the first periodic pattern image to produce at least one second periodic pattern image, a radiation image detector for detecting the second periodic pattern image to produce image data, and a phase shift differential image generator for producing a phase shift differential image based on the image data, comprises a data producing step, an added image producing step, and a corrected image producing step. In the data producing step, one or more boundaries, at each of which a value changes from $\pi/2$ to $-\pi/2$ or from $-\pi/2$ to $\pi/2$, are obtained in each of a first phase shift differential image, produced by the phase shift differential image generator in the absence of a subject in preliminary imaging, and a second phase shift differential image, produced by the phase shift differential image generator in the presence of the subject in main imaging. First staircase data and second staircase data, each changing by $\pi$ or $-\pi$ when crossing the boundary in a predetermined direction, is produced. In the added image producing step, the first staircase data is added to the first phase shift differential image to produce a first added phase shift differential image. The second staircase data is added to the second phase shift differential image to produce a second added phase shift differential image. In the corrected image producing step, the first added phase shift differential image is subtracted from the second added phase shift differential image to produce a corrected phase shift differential image.

According to the present invention, the first and second staircase data is added to the first and second phase shift differential images, respectively. Thereby, each of the first and second added phase shift differential images has a continuous profile. Because of this, artifact which is caused by a change in grating position between the preliminary and main imaging does not occur in the corrected phase shift differential image produced by subtraction of the first added phase shift differential image from the second added phase shift differential image.

BRIEF DESCRIPTION OF DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 9 is a flowchart illustrating operation of the X-ray imaging system in preliminary imaging;

FIG. 16 is a schematic view illustrating a configuration of an X-ray image detector used in a fourth embodiment of the present invention;

FIG. 17A is a graph of a profile of a phase shift differential image obtained in the preliminary imaging;

FIG. 17B is a graph of a profile of a phase shift differential image when there is a change in grating position between the preliminary and main imaging; and FIG. 17C illustrates a graph representing a subtraction image obtained from the phase shift differential images of FIGS. 17A and 17B.

DESCRIPTION OF THE PREFERRED EMBODIMENTS

First Embodiment

Figure 1:
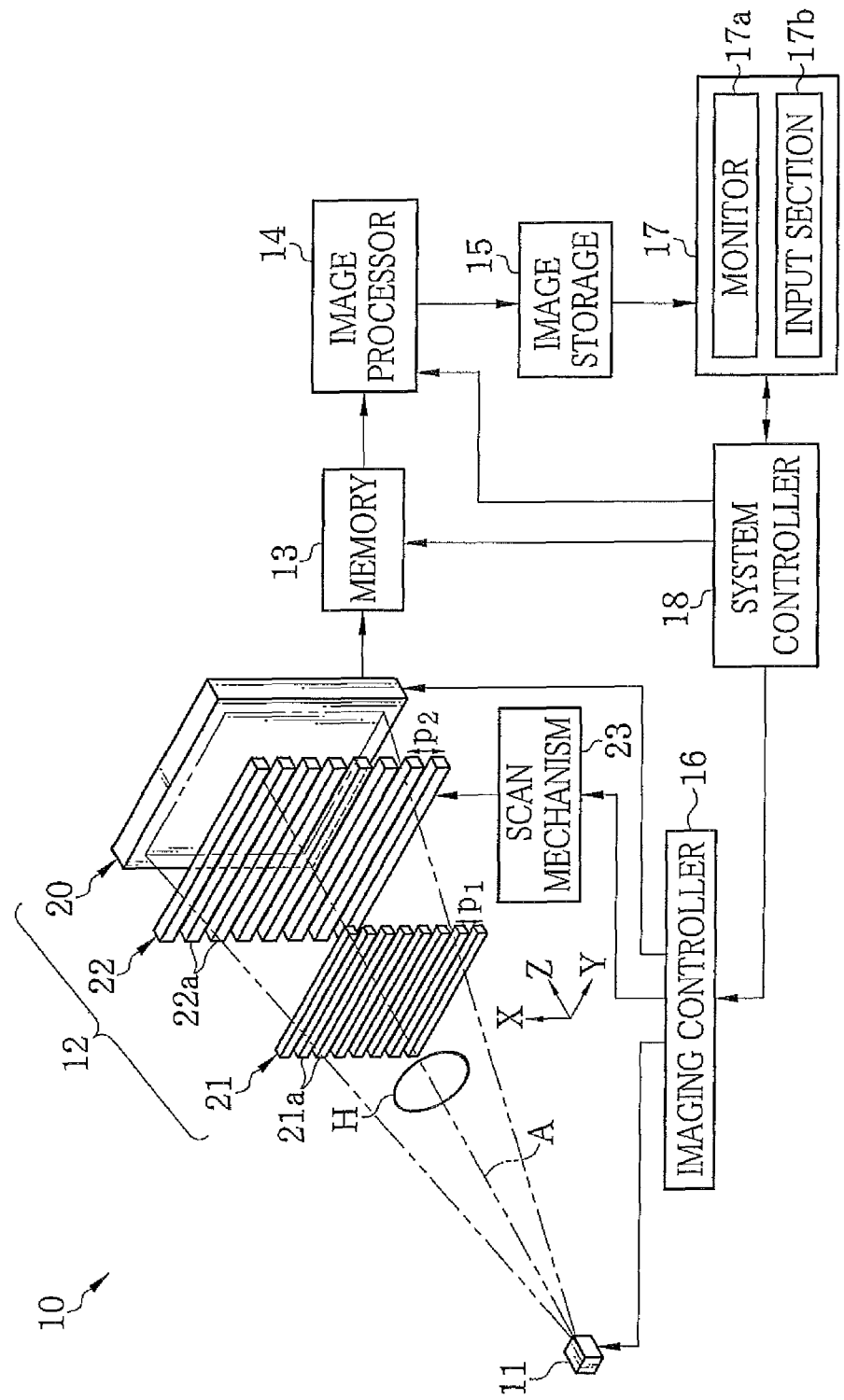
FIG. 1 is a schematic view illustrating a configuration of an X-ray imaging system according to a first embodiment of the present invention.

In FIG. 1, an X-ray imaging system 10 according to a first embodiment of the present invention is provided with an X-ray source 11, an imaging unit 12, a memory 13, an image processor 14, image storage 15, an imaging controller 16, a console 17, and a system controller 18. The X-ray source 11 irradiates a subject H with X-rays. The imaging unit 12 is disposed to face the X-ray source 11, and detects the X-rays, emitted from the X-ray source 11 and passed through the subject H, to produce image data. The memory 13 stores the image data read out from the imaging unit 12. The image processor 14 performs image processing on the pieces of image data, stored in the memory 13, to produce a phase contrast image. The image storage 15 stores the phase contrast image produced by the image processor 14. The imaging controller 16 controls the X-ray source 11 and the imaging unit 12. The console 17 is provided with a monitor 17a and an input section 17b. The system controller 18 controls the whole X-ray imaging system 10 based on an operation signal inputted from the input section 17b.

The X-ray source 11 is composed of a high voltage generator, an X-ray tube, a collimator (all not shown), and the like, and irradiates the subject H with the X-rays based on control of the imaging controller 16. For example, the X-ray tube is a rotating anode type, and releases electron beams from a filament in accordance with voltage applied from the high voltage generator. The X-ray tube generates the X-rays when the anode rotating at a predetermined speed is struck by the electron beams. The anode is rotated to reduce deterioration at a spot bombarded by the electron beams. The spot on the anode struck by the electron beams is an X-ray focal point where the X-rays are generated. The collimator restricts an X-ray field of the X-rays emitted from the X-ray tube so as to block the X-rays not directed toward a region of examination of the subject H.

The imaging unit 12 is provided with a flat panel detector (FPD) 20 composed of a semiconductor circuit, and a first absorption-type grating 21 and a second absorption-type grating 22. The first absorption-type grating 21 and the second absorption-type grating 22 detect a phase shift (angular change) of the X-rays, caused by the subject H, to perform phase imaging. The FPD 20 is disposed such that its detection surface is orthogonal to a direction (hereinafter referred to as the Z direction) along an optical axis A of the X-rays emitted from the X-ray source 11.

The first absorption-type grating 21 has a plurality of X-ray shielding portions (high X-ray absorption portions) 21a extending in a direction (hereinafter referred to as the Y direction) in a plane orthogonal to the Z direction and arranged at a predetermined pitch $p_1$ in a direction (hereinafter referred to as the X direction) orthogonal to the Z and Y directions. In a similar manner, the second absorption-type grating 22 has a plurality of X-ray shielding portions (high X-ray absorption portions) 22a extending in the Y direction and arranged at a predetermined pitch $p_2$ in the X direction. Metal with high X-ray absorption properties is preferable as a material of the X-ray shielding portions 21a and 22a. For example, gold (Au) and platinum (Pt) are preferable.

The imaging unit 12 is provided with a scan mechanism 23 that translationally moves the second absorption-type grating 22 in a direction (X direction) orthogonal to a direction (Y direction) of a grating line so as to change a position of the second absorption-type grating 22 relative to that of the first absorption-type grating 21. The scan mechanism 23 is composed of an actuator such as a piezoelectric element. The scan mechanism 23 is driven and controlled by the imaging controller 16 during fringe scanning which will be described below. The memory 13 stores the image data obtained with the imaging unit 12 in respective scanning steps (scan positions) of the fringe scanning, which will be detailed below. Note that the second absorption-type grating 22 and the scan mechanism 23 constitute an intensity modulator.

Figure 2:
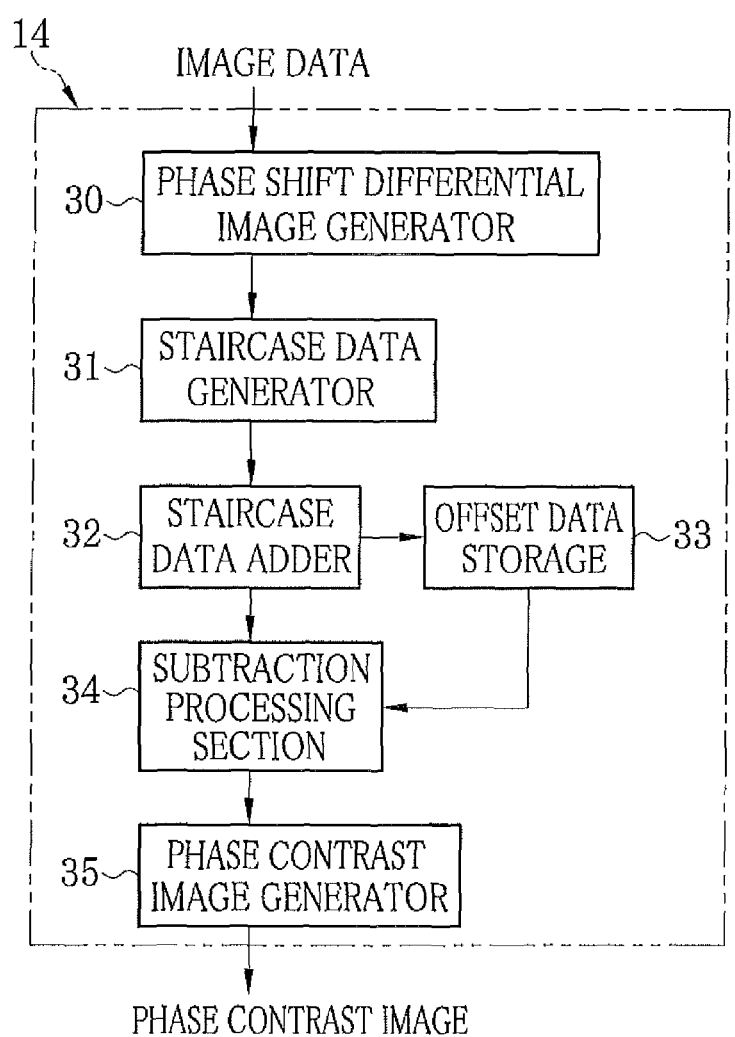
FIG. 2 is a block diagram illustrating a configuration of an image processor.

In FIG. 2, the image processor 14 is provided with a phase shift differential image generator 30, a staircase data generator 31, a staircase data adder 32, offset data storage 33, a subtraction processing section 34, and a phase contrast image generator 35. The phase shift differential image generator 30 produces a phase shift differential image based on the pieces of image data obtained with the imaging unit 12 in the respective scanning steps of the fringe scanning using the scan mechanism 23 and stored in the memory 13.

The staircase data generator 31 obtains or determines boundaries in the phase shift differential image produced by the phase shift differential image generator 30. A phase shift value, which will be described below, changes or jumps from $\pi/2$ to $-\pi/2$ or from $-\pi/2$ to $\pi/2$ when crossing each of the boundaries in the X direction. The staircase data generator 31 produces staircase data (or stepwise data) that changes by $\pi$ or $-\pi$ when crossing each of the boundaries in the X direction. The staircase data adder 32 adds the staircase data, produced by the staircase data generator 31, to the phase shift differential image. Hereinafter, the phase shift differential image added with the staircase data is referred to as the added phase shift differential image.

Figure 3A:
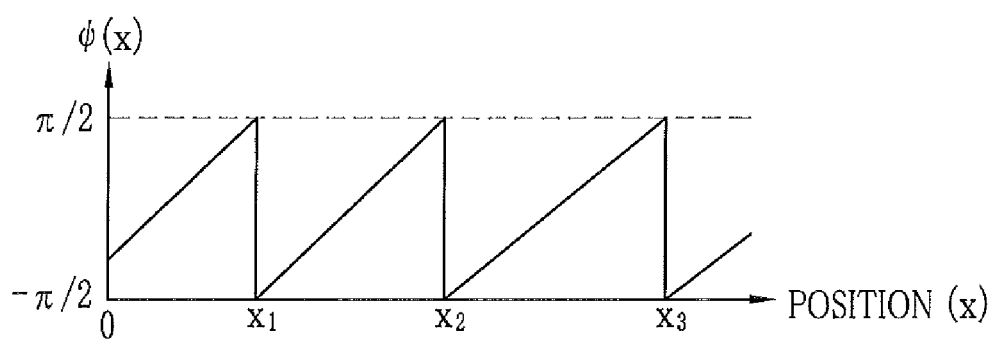
FIG. 3A is a graph of a profile of a phase shift differential image.
Figure 3B:
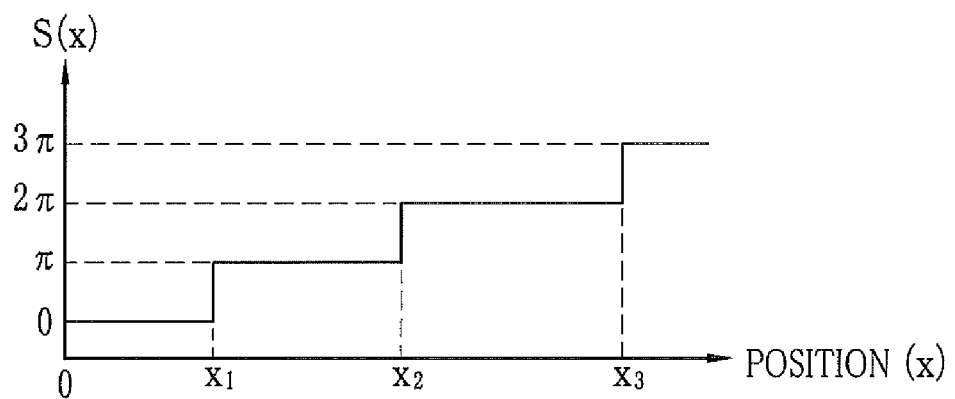
FIG. 3B is a graph of staircase data.
Figure 3C:
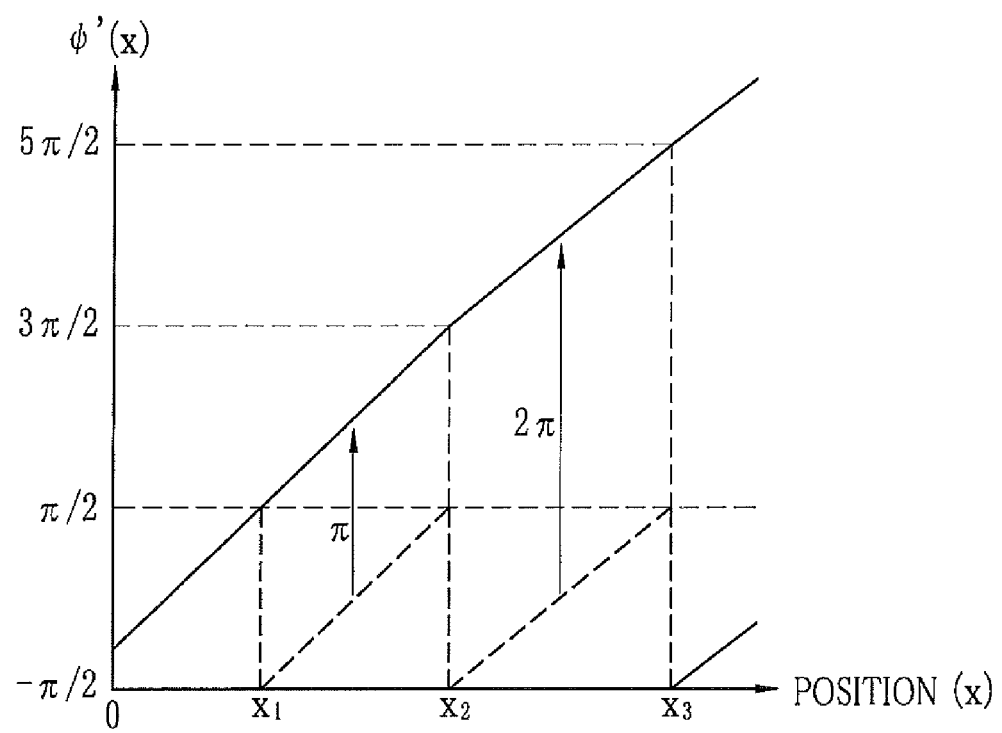
FIG. 3C is a graph of a profile of an added phase shift differential image.

In FIG. 3A, positions $x_1$, $x_2$, and $x_3$ show the positions of the respective boundaries in the phase shift differential image. The profile $\psi(x)$ of the phase shift differential image in the X direction changes from $\pi/2$ to $-\pi/2$ when crossing each of the positions (boundaries) $x_1$, $x_2$, and $x_3$. As shown in FIG. 3B, staircase data S(x) produced by the staircase data generator 31 is "0" where $0 \leq x < x_1$, "$\pi$" where $x_1 \leq x < x_2$, "$2\pi$" where $x_2 \leq x < x_3$, and "$3\pi$" where $x_3 \leq x$. As shown in FIG. 3C, the profile $\psi'(x)$ of the added phase shift differential image, added with the staircase data S(x) by the staircase data adder 32, in the X direction is substantially linear, increasing monotonically in the X direction.

Figure 4A:
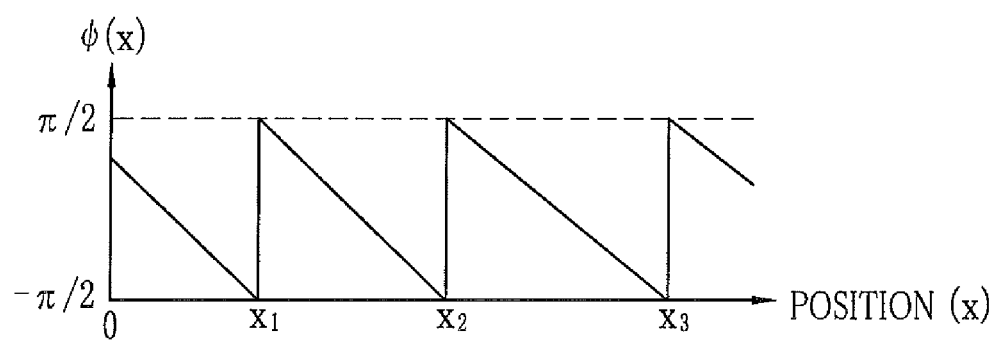
FIG. 4A is a graph of a profile of a phase shift differential image.
Figure 4B:
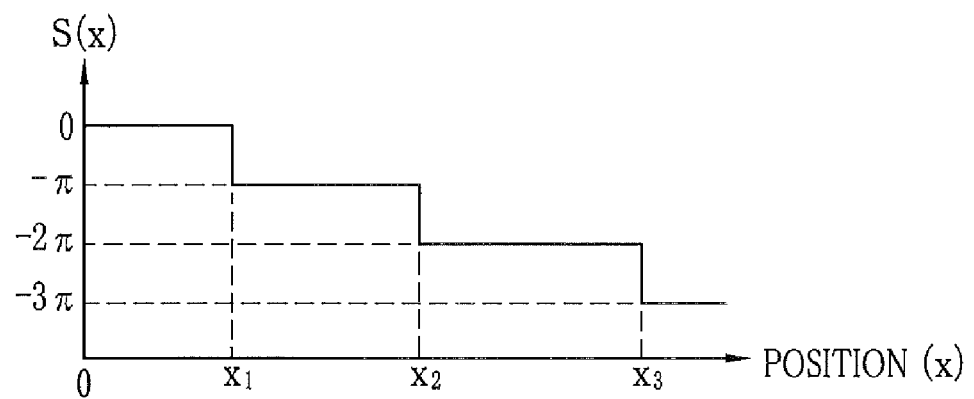
FIG. 4B is a graph of staircase data.
Figure 4C:
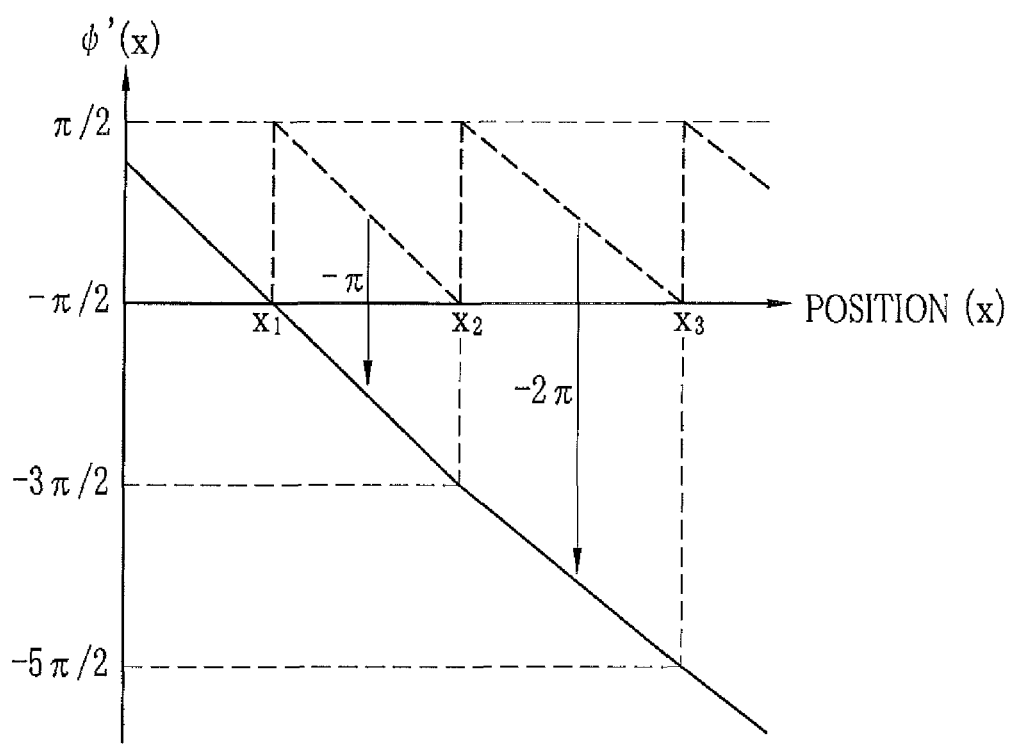
FIG. 4C is a graph of a profile of an added phase shift differential image.

In FIG. 4A, positions $x_1$, $x_2$, and $x_3$ show the positions of the respective boundaries in the phase shift differential image. The profile $\psi(x)$ of the phase shift differential image in the X direction jumps from $-\pi/2$ to $\pi/2$ when crossing each of the positions (boundaries) $x_1$, $x_2$, and $x_3$. As shown in FIG. 4B, the staircase data S(x) produced by the staircase data generator 31 is "0" where $0 \leq x < x_1$, "$-\pi$" where $x_1 \leq x < x_2$, "$-2\pi$" where $x_2 \leq x < x_3$, and "$-3\pi$" where $x_3 \leq x$. As shown in FIG. 4C, the profile $\psi'(x)$ of the added phase shift differential image, added with the staircase data S(x) by the staircase data adder 32, in the X direction is substantially linear, decreasing monotonically in the X direction.

In FIG. 2, the offset data storage 33 stores the added phase shift differential image (hereinafter referred to as the first added phase shift differential image) as offset data. In the preliminary imaging in the absence of the subject H between the X-ray source 11 and the imaging unit 12, the phase shift differential image generator 30 produces the phase shift differential image (hereinafter referred to as the first phase shift differential image). The staircase data adder 32 adds the staircase data (hereinafter referred to as the first staircase data), produced by the staircase data generator 31 based on the first phase shift differential image, to the first phase shift differential image. Thereby, the first added phase shift differential image is produced. The offset data storage 33 is composed of a volatile memory device such as a flash memory.

In the main imaging performed in the presence of the subject H between the X-ray source 11 and the imaging section 12, the phase shift differential image generator 30 produces a phase shift differential image (hereinafter referred to as the second phase shift differential image). The staircase data generator 31 produces the staircase data (hereinafter referred to as the second staircase data) based on the second phase shift differential image. The staircase data adder 32 adds the second staircase data to the second phase shift differential image. Thereby, a second added phase shift differential image is produced. The second added phase shift differential image is inputted to the subtraction processing section 34.

In the preliminary imaging, the system controller 18 allows the offset data storage 33 to store the first added phase shift differential image, produced by the staircase data adder 32, based on an imaging instruction inputted from the input section 17b of the console 17. In the main imaging, the system controller 18 controls the staircase data adder 32 to input the second added phase shift differential image, produced by the staircase data adder 32, to the subtraction processing section 34. The system controller 18 reads out the first added phase shift differential image stored in the offset data storage 33 and inputs it to the subtraction processing section 34.

The subtraction processing section 34 performs offset correction in which the first added phase shift differential image is subtracted from the second added phase shift differential image. Hereinafter, a phase shift differential image after the offset correction is referred to as the corrected phase shift differential image. The corrected phase shift differential image is inputted to the phase contrast image generator 35.

The phase contrast image generator 35 integrates the corrected phase shift differential image in the scan direction (X direction) to produce a phase contrast image. The phase contrast image, produced by the phase contrast image generator 35, is stored in the image storage 15, and then outputted to the console 17 and displayed on the monitor 17a.

The input section 17b of the console 17 allows an operator to input imaging instructions and contents thereof. For example, a switch, a touch panel, a mouse, or a keyboard may be used as the input section 17b. X-ray imaging conditions such as a tube voltage of the X-ray tube and X-ray exposure time, and imaging timing are inputted using the input section 17b. The monitor 17a is composed of an LCD or a CRT display, and displays the phase contrast image and text such as the X-ray imaging conditions.

Figure 5:
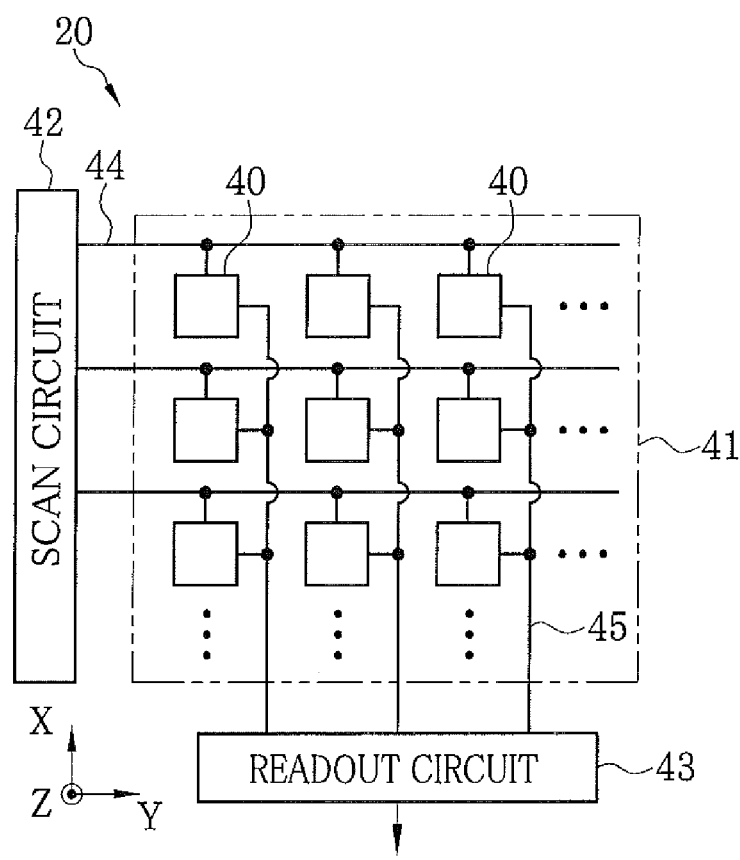
FIG. 5 is a schematic view illustrating a configuration of a flat panel detector.

In FIG. 5, the FPD 20 is composed of an image receiver 41, a scan circuit 42, and a readout circuit 43. The image receiver 41 is composed of an active matrix substrate and a plurality of pixels 40 arranged in two dimensions in the X and Y directions over the active matrix substrate. The pixels 40 convert the X-rays into charge and store the charge. The scan circuit 42 controls readout timing of the charge from the pixels 40. The readout circuit 43 reads out the charge from the pixels 40 and converts the charge into image data and outputs the image data. Note that the pixels 40 are connected to the scan circuit 42 through scanning lines 44 provided to respective rows of the pixels 40. The pixels 40 are connected to the read-out circuit 43 through signal lines 45 provided to respective columns of the pixels 40. An arrangement pitch of the pixels 40 is in the order of 100 µm in each of the X and Y directions.

The pixel 40 is a direct conversion-type X-ray detection element that converts the X-rays directly into the charge through a conversion layer (not shown) of amorphous selenium, or the like. The pixel 40 accumulates the charge in a capacitor (not shown) connected to an electrode below the conversion layer. Each pixel 40 is provided with a TFT switch (not shown). A gate electrode of the TFT switch is connected to the scanning line 44. A source electrode is connected to the capacitor. A drain electrode is connected to the signal line 45. When the TFT switch is turned on by a drive pulse from the scan circuit 42, the charge accumulated in the capacitor is read out through the signal line 45.

Note that the pixel 40 may be an indirect conversion type X-ray detection element that converts the X-rays into visible light using a scintillator (not shown) made from gadolinium oxide ($Gd_2O_3$), cesium iodide (CsI), or the like, and then converts the visible light into the charge using a photodiode (not shown), and accumulates the charge. In this embodiment, the radiation image detector is the FPD having a TFT panel by way of example. The radiation image detector is not limited to this. Various types of radiation image detectors having solid state imaging devices such as CCD image sensors and CMOS image sensors may be used.

The read-out circuit 43 is composed of integrating amplifiers, a correction circuit, A/D converters, and the like (all not shown). The integrating amplifier integrates the charge, outputted from the pixels 40 through the signal line 45, and converts the integrated charge into a voltage signal (image signal). The A/D converter converts the image signal, converted by the integrating amplifier, into digital image data. The correction circuit performs dark current correction, gain correction, linearity correction, and the like on the image data and inputs the corrected image data to the memory 13.

Figure 6:
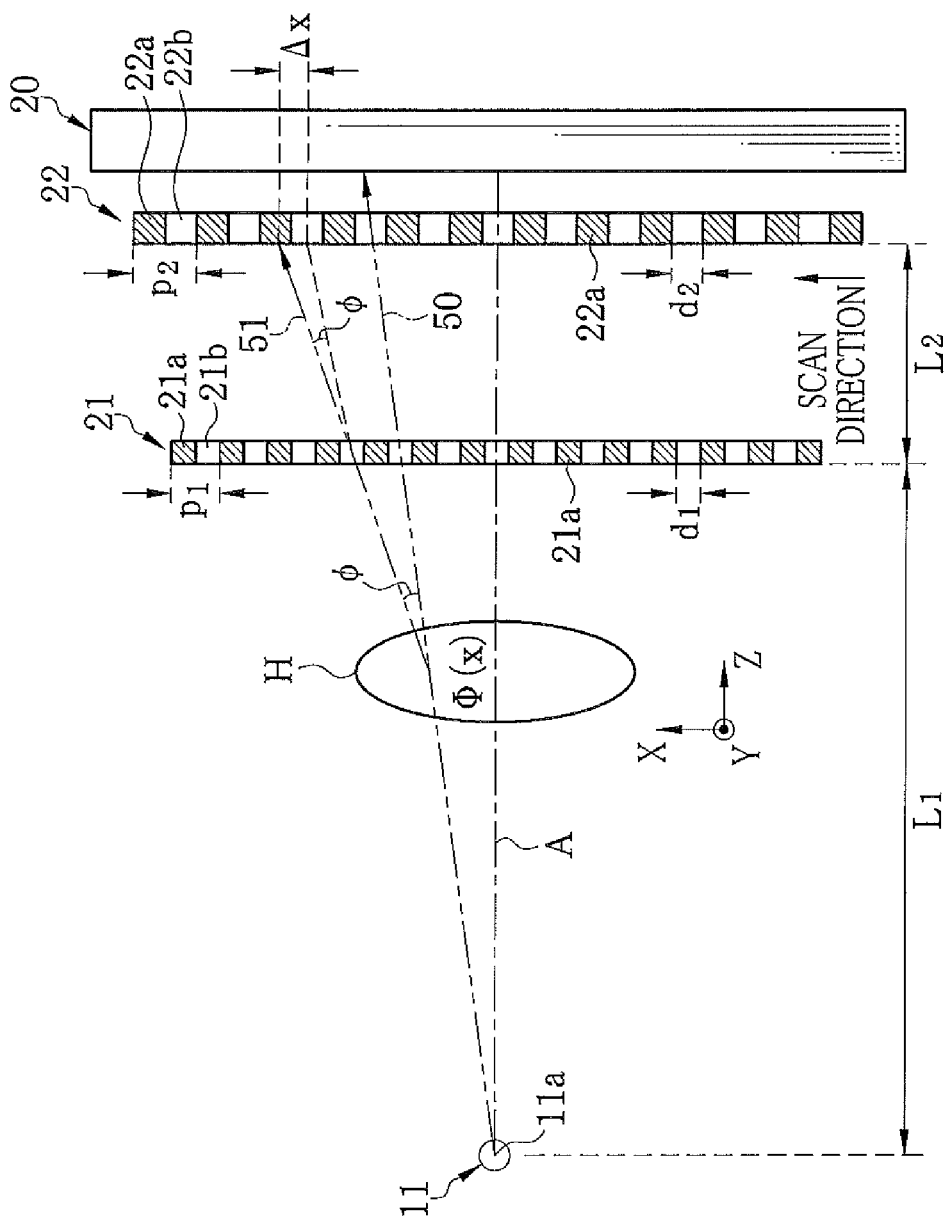
FIG. 6 is a schematic lateral view illustrating configurations of first and second absorption-type gratings.

In FIG. 6, the X-ray shielding portions 21a of the first absorption-type grating 21 are arranged in the X direction at a pitch $p_1$ and with a space $d_1$ between each other. A low X-ray absorption portion 21b is provided in each space $d_1$. In a similar manner, the X-ray shielding portions 22a of the second absorption-type grating 22 are arranged in the X direction at a pitch $p_2$ and with a space $d_2$ between each other. A low X-ray absorption portion 22b is provided in each space $d_2$. The first and second absorption-type gratings 21 and 22 do not provide phase shifts, but provide intensity changes to the incident X-rays. The first and second absorption-type gratings 21 and 22 are also referred to as amplitude-type gratings. It is preferable that the low X-ray absorption portions 21b and 22b are made from silicon (Si) or polymer, for example. Alternatively, the low X-ray absorption portions 21b and 22b may be gaps.

The first and the second absorption-type gratings 21 and 22 are configured to project the X-rays, passed through the low X-ray absorption portions 21b and 22b, in a linear (geometrical-optical) manner. To be more specific, each of the spaces $d_1$ and $d_2$ is made sufficiently larger than a peak wavelength of the X-rays emitted from the X-ray source 11. Thereby, most of the emission X-rays pass through the low X-ray absorption portions 21b and 22b in straight lines without diffraction. For example, when the rotating anode of the above-described X-ray tube is made from tungsten and the tube voltage is set to 50 kV, the peak wavelength of the X-rays is approximately 0.4 Å. In this case, most of the X-rays are projected linearly with no diffraction through the low X-ray absorption portions 21b and 22b when each of the spaces $d_1$ and $d_2$ is in the order of 1 to 10 µm. Each of the grating pitches $p_1$ and $p_2$ is in the order of 2 to 20 µm.

Because the X-ray source 11 does not emit parallel beams, but emits cone-shaped X-ray beams from an X-ray focal point 11a, being a light emission point, a first periodic pattern image (hereinafter referred to as the G1 image) formed by the X-rays passed through the first absorption-type grating 21 is enlarged in proportion to a distance from the X-ray focal point 11a. The grating pitch $p_2$ and the space $d_2$ of the second absorption-type grating 22 are determined such that a pattern of the low X-ray absorption portions 22b substantially coincides with a periodic pattern of bright areas in the G1 image at the position of the second absorption-type grating 22. Namely, the grating pitch $p_2$ and the space $d_2$ are determined to satisfy expressions (1) and (2), where $L_1$ denotes a distance between the X-ray focal point 11a and the first absorption-type grating 21, and $L_2$ denotes a distance between the first absorption-type grating 21 and the second absorption-type grating 22.

$$p_2 = \frac{L_1 + L_2}{L_1} p_1 \tag{1}$$

$$d_2 = \frac{L_1 + L_2}{L_1} d_1 \tag{2}$$

When a Talbot interferometer is used, the distance $L_2$ between the first absorption-type grating 21 and the second absorption-type grating 22 is restricted by the Talbot length. The Talbot length is determined by the grating pitch of the first diffraction grating and the X-ray wavelength. In the imaging unit 12 of this embodiment, however, the first absorption-type grating 21 is configured to project the incident X-rays without causing diffraction. Because the G1 image of the first absorption-type grating 21 is obtained, proportionally, at any position behind the first absorption-type grating 21, the distance $L_2$ can be set irrespective of the Talbot length.

As described above, the imaging unit 12 of this embodiment does not constitute the Talbot interferometer. However, when assuming that the X-rays are diffracted by the first absorption-type grating 21 to produce the Talbot effect, a Talbot length $Z_m$ is represented by an expression (3) using the grating pitch $p_1$ of the first absorption-type grating 21, the grating pitch $p_2$ of the second absorption-type grating 22, the X-ray wavelength (peak wavelength) $\lambda$, and a positive integer m.

$$Z_m = m \frac{p_1 p_2}{\lambda} \tag{3}$$

The expression (3) represents the Talbot length on condition that the X-ray source 11 emits the cone-shaped X-rays. The expression (3) is disclosed in "Atsushi Momose et al., Japanese Journal of Applied Physics, Vol. 47, No. 10, October 2008, page 8077".

In this embodiment, as described above, the distance $L_2$ can be set irrespective of the Talbot length $Z_m$. To reduce the thickness of the imaging unit 12 in the Z direction, the distance $L_2$ is set shorter than a minimum Talbot length $Z_1$ (when m=1). Namely, the distance $L_2$ is set to a value within a range satisfying an expression (4).

$$L_2 < \frac{p_1 p_2}{\lambda} \quad (4)$$

To produce a periodic pattern image with high contrast, it is preferable that the X-ray shielding portions 21a and 22a completely block (absorb) the X-rays. However, even if the above-mentioned material (gold, platinum, or the like) with high X-ray absorption properties is used, the X-rays passing through the X-ray shielding portions 21a and 22a still exist. To improve the X-ray shielding properties, it is preferable to increase the thickness (in the Z direction) of each of the X-ray shielding portions 21a and 22a (namely, to increase an aspect ratio) as much as possible. For example, it is preferable to block 90% or more of the emission X-rays when the tube voltage of the X-ray tube is 50 kV. It is preferable that the thickness of each of the X-ray shielding portions 21a and 22a is in the range of 10 μm to 200 μm.

With the use of the above-configured first and second absorption-type gratings 21 and 22, the G1 image produced with the first absorption-type grating 21 is partly blocked by the superposition of the G1 image onto the second absorption-type grating 22 and thereby subjected to the intensity modulation. Thus, a second periodic pattern image (hereinafter referred to as the G2 image) is produced. The G2 image is captured with the FPD 20.

There is a slight difference between a pattern period of the G1 image at the position of the second absorption-type grating 22 and the grating pitch $p_2$ of the second absorption-type grating 22 due to arrangement error or the like. Due to this minute difference, moiré fringes occur in the G2 image. When the grating arrangement directions of the first and second absorption-type gratings 21 and 22 are not the same due to error in grating arrangement directions of the first and second absorption-type gratings 21 and 22, so-called rotational moiré fringes occur in the G2 image. The rotational moiré fringes do not cause any problem when a period of the moiré fringes in the X or Y direction is greater than an arrangement pitch of the pixels 40.

When the subject H is disposed between the X-ray source 11 and the first absorption-type grating 21, the G2 image detected with the FPD 20 is modulated by the subject H. An amount of the modulation is in proportion to an angle of the X-rays shifted due to refraction effect of the subject H. The phase contrast image of the subject H is produced by analyzing the G2 image detected with the FPD 20.

Next, a method for analyzing the G2 image is described in principle. FIG. 6 illustrates an X-ray beam refracted in accordance with phase shift distribution $\Phi(x)$ relative to the X direction of the subject H byway of example. A numeral 50 denotes a path of an X-ray beam traveling linearly in the absence of the subject H. The X-ray beam traveling along the path 50 passes through the first and the second absorption-type gratings 21 and 22, and then is incident on the FPD 20. In the presence of the subject H, a numeral 51 denotes a path of the X-ray beam shifted by the refraction of the subject H. The X-ray beam traveling along the path 51 passes through the first absorption-type grating 21, but then is blocked by the X-ray shielding portion 22a of the second absorption-type grating 22.

The phase shift distribution $\Phi(x)$ of the subject H is represented by an expression (5), where n(x, z) denotes refractive index distribution of the subject H, and z denotes a direction in which the X-rays travel or are transmitted.

$$\Phi(x) = \frac{2\pi}{\lambda} \int [1 - n(x, z)] dz \quad (5)$$

The G1 image, projected from the first absorption-type grating 21 onto the position of the second absorption-type grating 22, is displaced in the X direction by an amount corresponding to a refraction angle ϕ due to the refraction of the X-rays at the subject H. A displacement amount Δx is represented approximately by an expression (6) on the basis that the refraction angle ϕ of the X-rays is minute.

$$\Delta x \approx L_2 \phi \quad (6)$$

The refraction angle ϕ is represented by an expression (7) using the X-ray wavelength λ and the phase shift distribution $\Phi(x)$ of the subject H.

$$\phi = \frac{\lambda}{2\pi} \frac{\partial \Phi(x)}{\partial x} \quad (7)$$

As described above, the displacement amount Δx of the G1 image, caused by the X-ray refraction at the subject H, relates to the phase shift distribution $\Phi(x)$ of the subject H. The displacement amount Δx relates to a phase shift value ψ of the intensity modulation signal of each of the pixels 40 detected with the FPD 20 as represented by an expression (8).

$$\psi = \frac{2\pi}{p_2} \Delta x = \frac{2\pi}{p_2} L_2 \phi \quad (8)$$

By obtaining the phase shift value ψ of the intensity modulation signal of each of the pixels 40, the refraction angle ϕ is calculated using the expression (8) and a differential value of the phase shift distribution $\Phi(x)$ is calculated using the expression (7). By integrating the differential value relative to x, the phase shift distribution $\Phi(x)$ of the subject H, that is, the phase contrast image of the subject H is produced.

In this embodiment, the phase shift differential image generator 30 produces both the phase shift differential image (first phase shift differential image) in the absence of the subject H and the phase shift differential image (second phase shift differential image) in the presence of the subject H. This is because the X-rays are refracted due to distortion, manufacturing error, arrangement error, or the like in the first absorption grating 21 and/or the second absorption gratings 22, even if in the absence of the subject H. The phase shift differential image generator 30 calculates the phase shift value ψ using the fringe scanning method described below. Thereby, the phase shift differential image generator 30 produces the first and second phase shift differential images.

In the fringe scanning method, the image is captured with one of the first and the second absorption-type gratings 21 and 22 translationally moved relative to the other in the X direction (namely, the image is captured with the phases of the grating periods of the first and second absorption-type gratings 21 and 22 changed). In this embodiment, the above-described scan mechanism 23 moves the second absorption-type grating 22. The moiré fringes in the G2 image move with the movement of the second absorption-type grating 22, and return to the original position when the translational distance (an amount of movement in the X direction) reaches one grating period (the grating pitch $p_2$) of the second absorption-type grating 22 (namely, when the phase shift reaches $2\pi$). Thus, the G2 image is captured using the FPD 20 every time the second absorption-type grating 22 is moved by an integral fraction of the grating pitch $p_2$. The intensity modulation signal of each pixel is obtained from the pieces of image data obtained from the image captures. The phase shift differential image generator 30 calculates the phase shift value $\psi$ of the intensity modulation signal on a pixel-by-pixel basis. The two-dimensional distribution of the phase shift value $\psi$ corresponds to the phase shift differential image.

Figure 7:
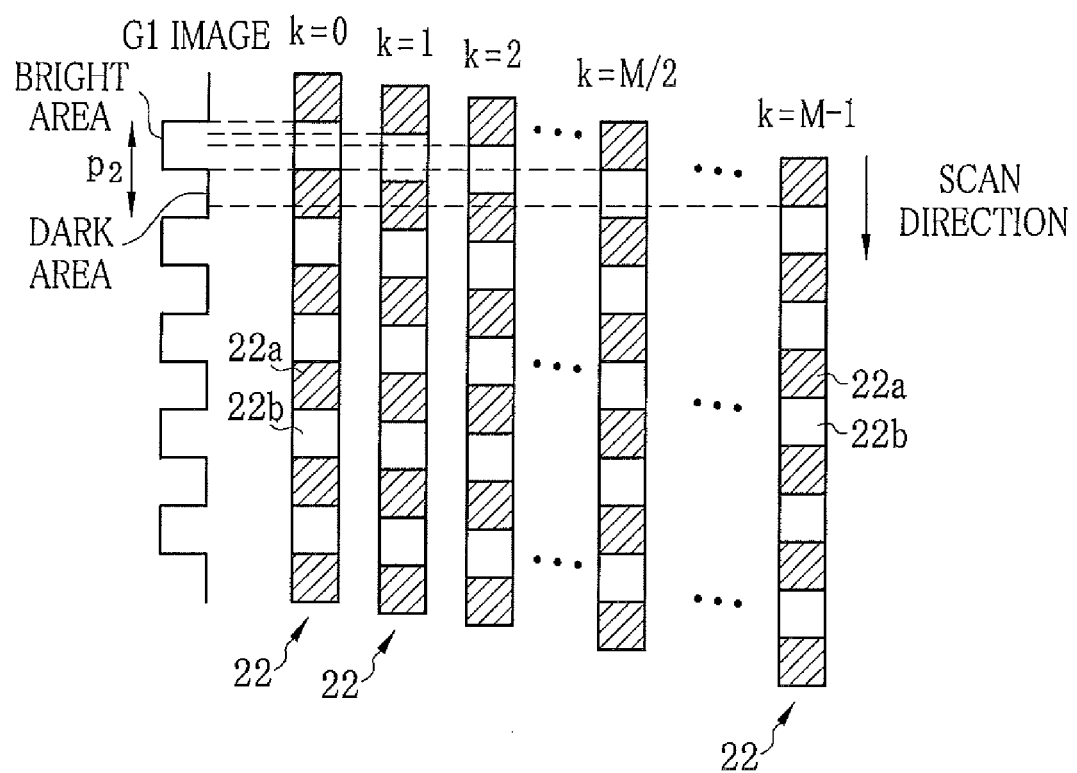
FIG. 7 is an explanatory view illustrating a fringe scanning method.

FIG. 7 schematically illustrates the second absorption-type grating 22 moved at a scanning pitch ($p_2$/M) obtained by dividing the grating pitch $p_2$ by a number M (an integer greater than or equal to 2). The scan mechanism 23 translationally moves the second absorption-type grating 22 to each of M scan positions (k=0, 1, 2, . . . , M−1) sequentially. Note that, in FIG. 7, an initial position of the second absorption-type grating 22 is a position (k=0) where dark areas of the G1 image at the position of the second absorption-type grating 22 substantially coincide with the X-ray shielding portions 22a in the absence of the subject H. Alternatively, the initial position may be any one of the positions (k=0, 1, 2, . . . , M−1).

First, at the position (k=0), mainly, a component (non-refractive component) of the X-rays not refracted by the subject H passes through the second absorption-type grating 22. Next, as the second absorption-type grating 22 is moved to each of the positions (k=1, 2, . . . ) sequentially, the non-refractive component decreases while a component (refractive component) of the X-rays refracted by the subject H increases in the X-rays passing through the second absorption-type grating 22. In particular, at the position (k=M/2), mainly and substantially only the refractive component passes through the second absorption-type grating 22. At the positions subsequent to the position (k=M/2), on the contrary, the refractive component decreases while the non-refractive component increases in the X-rays passing through the second absorption-type grating 22.

After the image is captured with the FPD 20 at each of the positions (k=0, 1, 2, . . . , M−1), the M pieces of pixel data are obtained per pixel 40. Hereinafter, a method for calculating the phase shift value $\psi$ based on the M pieces of pixel data (intensity modulation signal) is described. Pixel data $I_k(x)$ of each of the pixels 40 at the time the second absorption-type grating 22 is positioned at a position k is generally represented by an expression (9).

$$I_k(x) = A_0 + \sum_{n>0} A_n \exp\left[2\pi i \frac{n}{p_2}\left\{L_2\phi(x) + \frac{kp_2}{M}\right\}\right] \quad (9)$$

Here, x denotes a coordinate of the pixel in the X direction, $A_0$ denotes the intensity of the incident X-rays, $A_n$ denotes a value corresponding to the contrast of the intensity modulation signal, n denotes a positive integer, and i denotes an imaginary unit. The $\phi(x)$ denotes the refraction angle $\phi$ expressed as a function of the coordinate x of the pixel 40.

When a relational expression (10) is applied, the refraction angle $\phi(x)$ is represented by an expression (11).

$$\sum_{k=0}^{M-1} \exp\left(-2\pi i \frac{k}{M}\right) = 0 \quad (10)$$

$$\phi(x) = \frac{p_2}{2\pi L_2}\arg\left[\sum_{k=0}^{M-1} I_k(x)\exp\left(-2\pi i \frac{k}{M}\right)\right] \quad (11)$$

Here, arg[ ] represents extraction of argument and corresponds to the phase shift value $\psi(x)$ at the coordinate x as shown by an expression (12).

$$\psi(x) = \arg\left[\sum_{k=0}^{M-1} I_k(x)\exp\left(-2\pi i \frac{k}{M}\right)\right] \quad (12)$$

The phase shift value $\psi(x)$ is also expressed as an arctangent as shown by an expression (13).

$$\psi(x) = -\tan^{-1}\left[\frac{\sum_{k=0}^{M-1} I_k(x)\sin\left(-2\pi \frac{k}{M}\right)}{\sum_{k=0}^{M-1} I_k(x)\cos\left(-2\pi \frac{k}{M}\right)}\right] \quad (13)$$

Figure 8A:
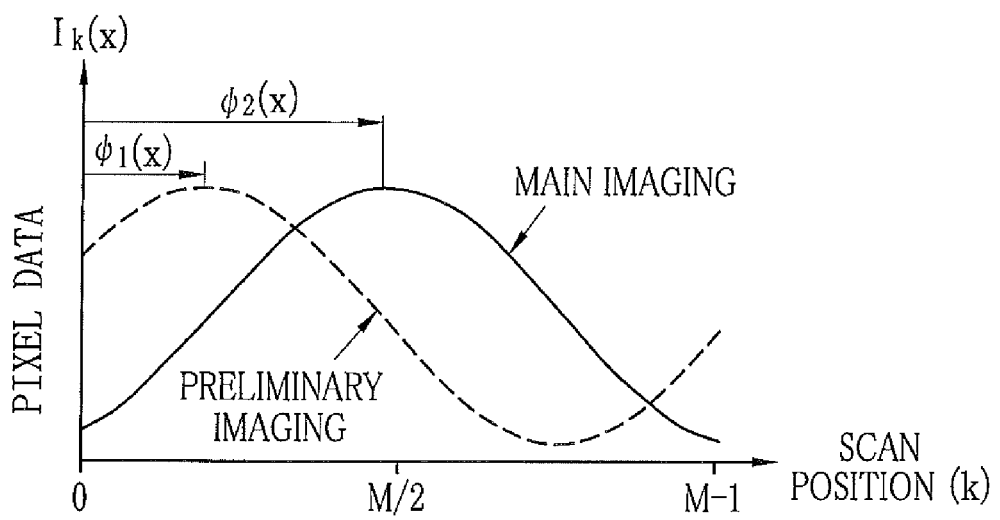
FIG. 8A is a graph illustrating an intensity modulation signal of a pixel on which X-rays passed through a subject are incident.
Figure 8B:
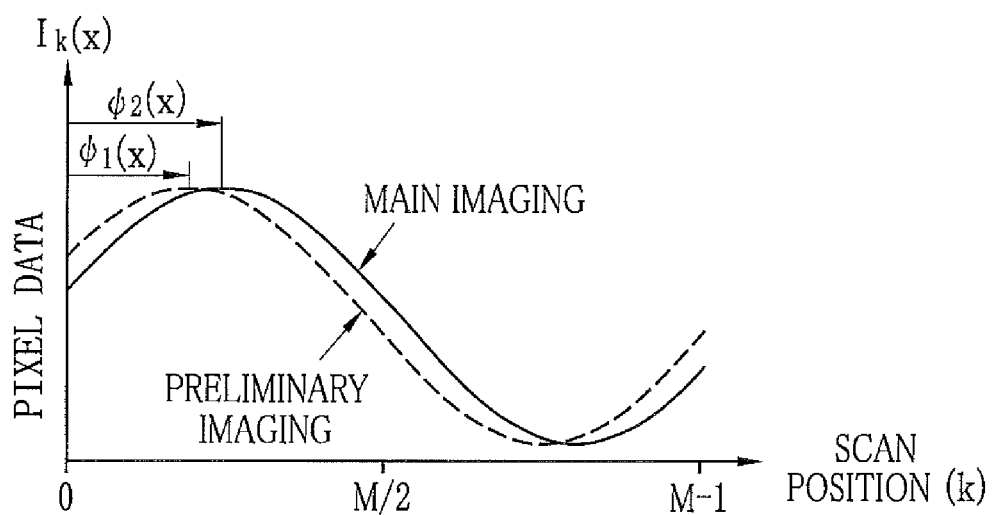
FIG. 8B is a graph illustrating an intensity modulation signal of a pixel in a directly-exposed area.

In FIGS. 8A and 8B, the pixel data $I_k(x)$ obtained from each of the pixels 40 varies periodically at a period of the grating pitch $p_2$ relative to the position k of the second absorption-type grating 22. A broken line in each of FIGS. 8A and 8B denotes the intensity modulation signal in the preliminary imaging, and has a phase shift value $\psi_1(x)$, by way of example. A solid line in each of FIGS. 8A and 8B denotes the intensity modulation signal in the main imaging, and has a phase shift value $\psi_2(x)$, by way of example. The phase shift value $\psi_1(x)$ occurred in the preliminary imaging is due to the distortion, the manufacturing error, the arrangement error, or the like in the first absorption-type grating 21 and/or the second absorption-type grating 22.

FIG. 8A shows the intensity modulation signals of the pixel 40 on which the X-rays passed through the subject H are incident, by way of example. There is a phase shift ($\psi_2(x)$−$\psi_1(x)$) between the intensity modulation signals caused by the subject H. FIG. 8B, on the other hand, shows the intensity modulation signals of the pixel 40 located in a directly-exposed area outside of the area in which the subject H is captured, by way of example. In this case, the value $\psi_2(x)$ is expected to be equal to the value $\psi_1(x)$ because the intensity modulation signals are not affected by the subject H. However, the phase shift occurs when there is a difference in positional relationship of the first and second absorption-type gratings 21 and 22 between the preliminary imaging and the main imaging.

For example, when an actuator such as a piezoelectric element is used as the scan mechanism 23, the scan pitch ($p_2$/M) is controlled relatively accurately. After scanning from the position k=0 to the position k=M−1, however, the second absorption-type grating 22 may not return to the initial position (k=0) accurately. There may be error in the order of several μm, which is not negligible, in the position of the second absorption-type grating 22. The error corresponds to the difference in positional relationship of the first and second absorption-type gratings 21 and 22 between the preliminary imaging and the main imaging.

In the above descriptions, a y coordinate in the Y direction of the pixel 40 is not considered. When calculation similar to the above is performed relative to the y coordinate, two-dimensional images $\psi_1(x, y)$ and $\psi_2(x, y)$ of the phase shift values are produced. The two-dimensional image $\psi_1(x, y)$ corresponds to the first phase shift differential image. The two-dimensional image $\psi_2(x, y)$ corresponds to the second phase shift differential image. Note that, in this embodiment, the phase shift differential image is expressed as the two-dimensional distribution of the phase shift value $\psi$ by way of example. Two-dimensional distribution of any physical quantity, for example, the refraction angle $\phi$ may be used as the phase shift differential image as long as the physical quantity is in proportional relation to the differential value of the phase shift distribution $\Phi(x, y)$.

Figure 10:
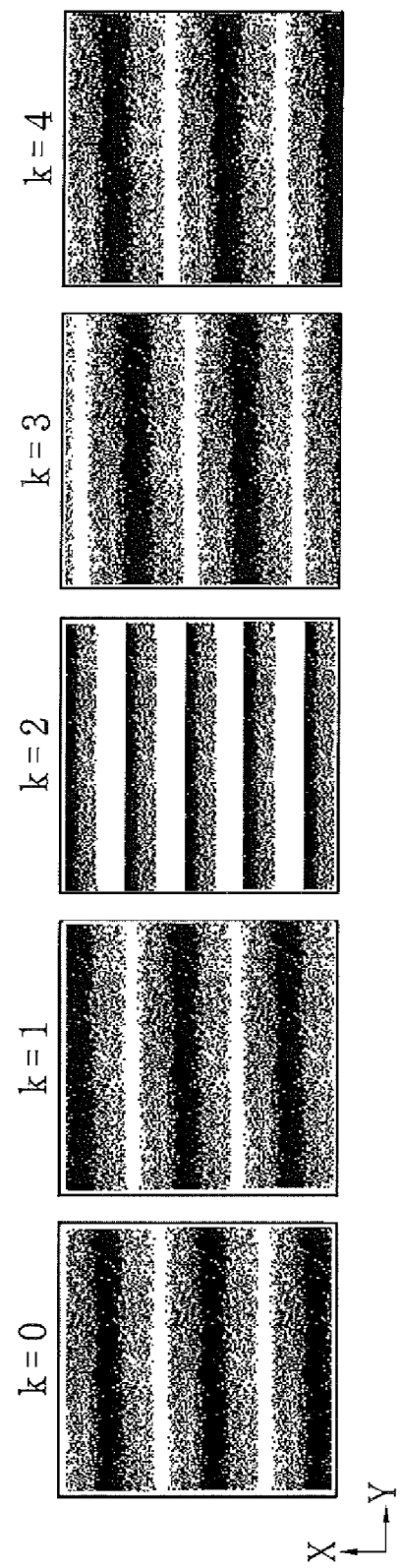
FIG. 10 illustrates image data obtained at each of scan positions.

Next, operation of the above configured X-ray imaging system 10 is described. As shown by the flowchart shown in FIG. 9, when an instruction to start the preliminary imaging is provided from the input section 17b of the console 17 (S10: YES), each section in the X-ray imaging system 10 operates in correlation with each other to perform the X-ray exposure from the X-ray source 11 and the detection operation of the FPD 20 at each scan position with the second absorption-type grating 22 moved thereto. Thereby, pieces of the image data are produced (S11). For example, when the number M of the scanning step is M=5, the exposure and the detection operation are performed in each of the scan positions k=0, 1, 2, 3, and 4. As shown in FIG. 10, the image data is obtained in each of the scan positions k. Each image data contains the above-described moiré fringes. The moiré fringes move in the X direction in accordance with a change in the scan position k. When the scan position k changes by one period corresponding to the grating pitch $p_2$, the moiré fringes return to the original position.

Figures 11A, 11B:
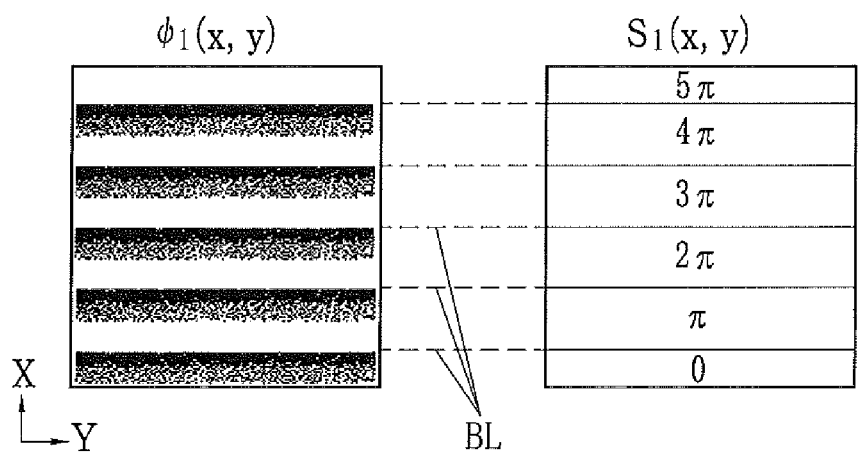
FIG. 11A illustrates a first phase shift differential image.
FIG. 11B illustrates first staircase data calculated with the origin of coordinate x located at a lower edge.

The image data is stored in the memory 13. The phase shift differential image generator 30 produces the first phase shift differential image $\psi_1(x, y)$ using the expression (13) (S12). As shown in FIG. 11A, the first phase shift differential image $\psi_1(x, y)$ has moiré fringes with ½ period of the moiré fringes of the above-described image data. In the moiré fringes shown in FIG. 11A, the value becomes closer to $\pi/2$ as the color of a portion in the moiré fringes gets darker (blacker). The value becomes closer to $-\pi/2$ as the color of a portion in the moiré fringes gets lighter (whiter). A portion at which the color changes from black to white in the X direction (upward from the bottom in the drawing) is the boundary BL at which the value changes from $\pi/2$ to $-\pi/2$. Then, as shown in FIG. 11B, the staircase data generator 31 produces first staircase data $S_1(x, y)$ based on the boundary BL (S13).

Figures 12A, 12B:
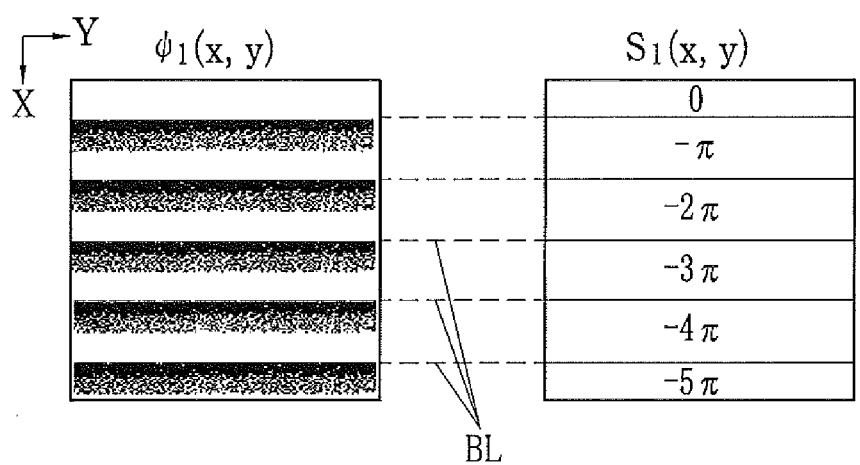
FIG. 12A illustrates a first phase shift differential image.
FIG. 12B illustrates first staircase data calculated with the origin of coordinate x located at an upper edge.

Note that in FIG. 11A, the boundary BL is determined by the search in the upward direction from the origin of the coordinate x located on the bottom edge. Conversely, as shown in FIG. 12A, the boundary BL may be determined by the search in a downward direction from the origin of the coordinate x located on the top edge. In this case, the value changes from $-\pi/2$ to $\pi/2$ at the boundary BL, so that the first staircase data $S_1(x, y)$ is produced as shown in FIG. 12B. The profiles in the X direction in FIGS. 11A and 11B correspond to the graphs in FIGS. 3A and 3B, respectively. The profiles in the X direction in FIGS. 12A and 12B correspond to the graphs in FIGS. 4A and 4B, respectively.

Then, the staircase data adder 32 adds the first staircase data $S_1(x, y)$ to the first phase shift differential image $\psi_1(x, y)$. Thereby, a first added phase shift differential image $\psi_1'(x, y)$ is produced (S14). The profile of the first added phase shift differential image $\psi_1'(x, y)$, produced based on FIGS. 11A and 11B, in the X direction is approximately linear as shown in FIG. 3C. The profile of the first added phase shift differential image $\psi_1'(x, y)$, produced based on FIGS. 12A and 12B, in the X direction is approximately linear as shown in FIG. 4C. The first added phase shift differential image $\psi_1'(x, y)$ is stored as the offset data in the offset data storage 33 (S15).

Thereby, the operation of the preliminary imaging is completed. The second absorption-type grating 22 is returned to the scan start position (initial position k=0) (S16). The operator is notified of the completion of the preliminary imaging via a message displayed on the monitor 17a, or the like (S17).

It is not necessary to perform the preliminary imaging every time before the main imaging. The preliminary imaging is performed as necessary at a startup of the X-ray imaging system 10, for example. When another preliminary imaging is performed subsequently, the existing offset data stored in the offset data storage 33 is overwritten by new offset data.

Figure 13:
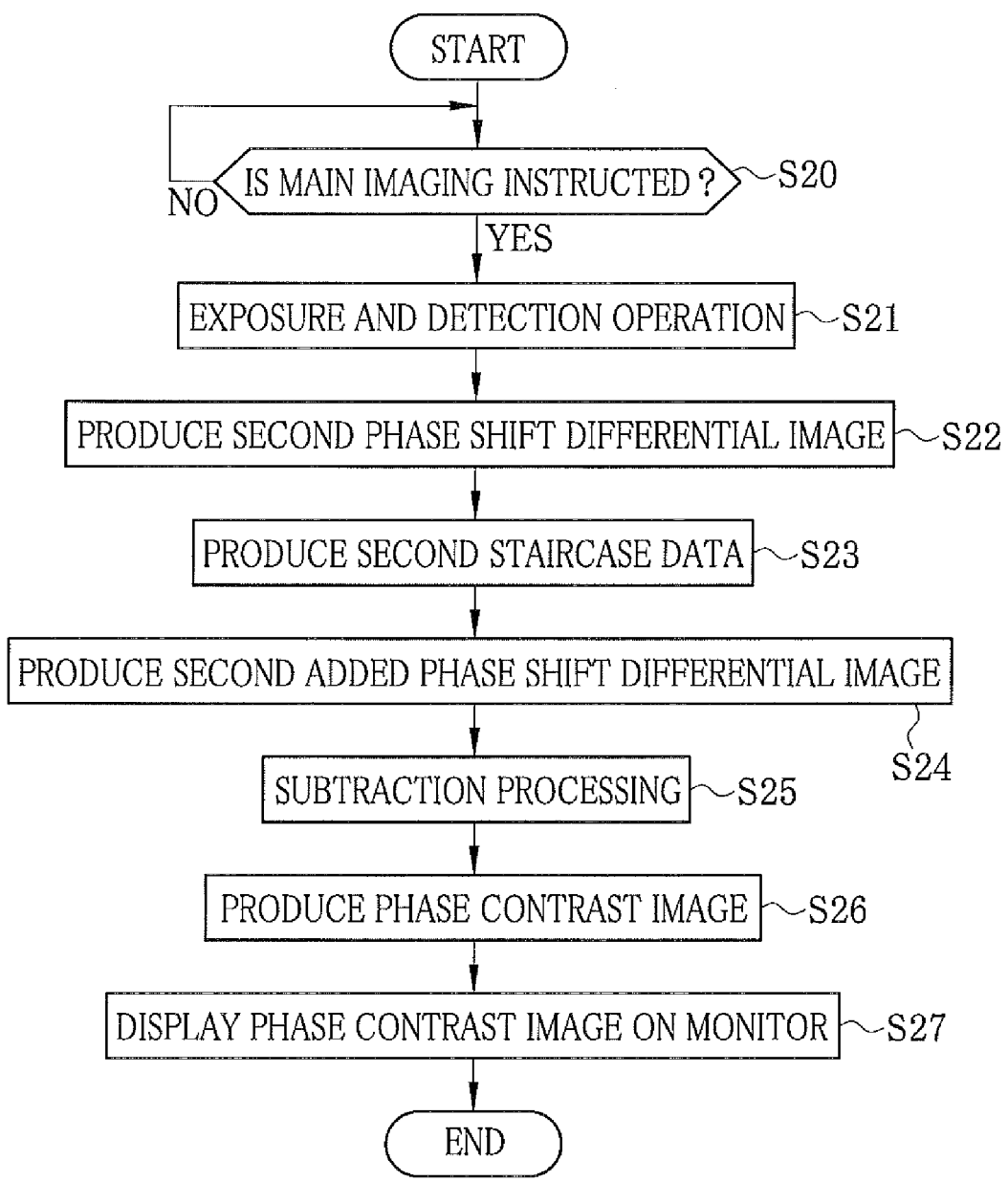
FIG. 13 is a flowchart illustrating operation of the X-ray imaging system in main imaging.

Next, the main imaging is performed in a state that the subject H is disposed between the X-ray source 11 and the first absorption-type grating 21. As shown by the flowchart in FIG. 13, when an instruction to start the main imaging is provided from the input section 17b of the console 17 (S20: YES), the X-ray exposure from the X-ray source 11 and the detection operation of the FPD 20 are performed at each scan position with the second absorption-type grating 22 moved thereto, in a manner similar to the preliminary imaging. Thereby, the pieces of image data are produced (S21).

The pieces of image data are stored in the memory 13. The phase shift differential image generator 30 produces the second phase shift differential image $\psi_2(x, y)$ using the expression (13) (S22). Similar to the first phase shift differential image $\psi_1(x, y)$, moiré fringes occur in the second phase shift differential image $\psi_2(x, y)$. Then, in a procedure similar to the preliminary imaging, the staircase data generator 31 produces second staircase data $S_2(x, y)$ (S23). The staircase data adder 32 adds the second staircase data $S_2(x, y)$ to the second phase shift differential image $\psi_2(x, y)$. Thereby, the second added phase shift differential image $\psi_2'(x, y)$ is produced (S24). The profile of the second added phase shift differential image $\psi_2'(x, y)$ in the X direction is approximately linear. Note that the refraction of the X-rays caused by the subject H affects the profile to the extent that the approximately linear profile is slightly distorted.

The second added phase shift differential image $\psi_2'(x, y)$ is inputted to the subtraction processing section 34, and the first added phase shift differential image $\psi_1'(x, y)$ is read out from the offset data storage 33 and inputted to the subtraction processing section 34. The subtraction processing section 34 performs the offset correction in which the first added phase shift differential image $\psi_1'(x, y)$ is subtracted from the second added phase shift differential image $\psi_2'(x, y)$. Thereby, the corrected phase shift differential image is produced (S25). Because the profiles of the first and second added phase shift differential images $\psi_1'(x, y)$ and $\psi_2'(x, y)$ in the X direction are approximately linear, the corrected phase shift differential image after the subtraction processing is free from the conventional artifact caused by a positional change in the first absorption-type grating 21 and/or second absorption-type grating 22 between the preliminary imaging and the main imaging.

The corrected phase shift differential image produced by the subtraction processing section 34 is inputted to the phase contrast image generator 35. The phase contrast image generator 35 integrates the corrected phase shift differential image in the X direction to produce the phase contrast image (S26). The phase contrast image is stored in the image storage 15, and then outputted to the console 17 and displayed on the monitor 17a (S27). Thereby, the operation of the main imaging is completed. Note that, instead of the phase contrast image, the corrected phase shift differential image can be stored in the image storage 15. The corrected phase shift differential image can be displayed on the monitor 17a.

Figures 14A, 14B:
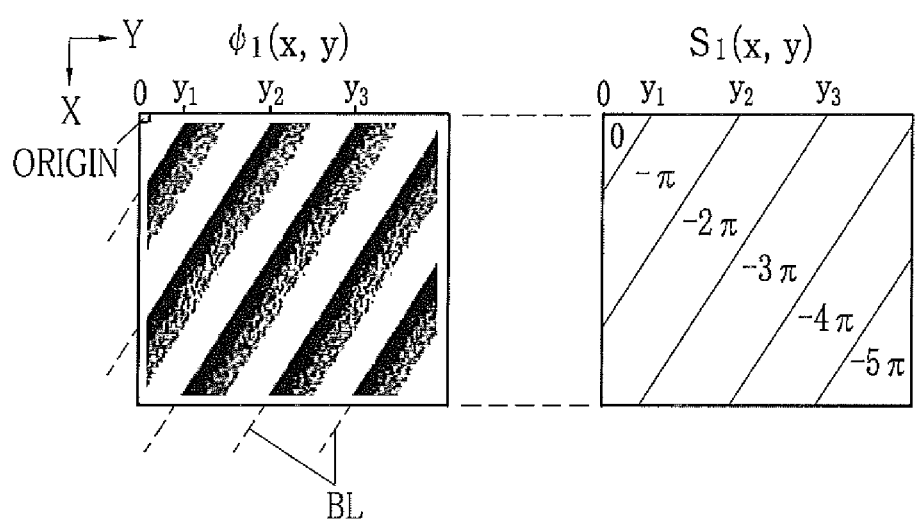
FIG. 14A illustrates a first phase shift differential image with rotational moiré fringes.
FIG. 14B illustrates first staircase data for the case illustrated in FIG. 14A.

Note that, in FIGS. 11A, 11B, 12A, and 12B, the boundaries BL of the moiré fringes are orthogonal to the scan direction (X direction) by way of example. As shown in FIG. 14A, when the first absorption-type grating 21 and/or the second absorption-type grating 22 has rotational error about the Z axis, the moiré fringes are rotated such that the boundaries BL are tilted relative to the Y direction. To produce appropriate staircase data even when the rotational moiré fringes occur, it is preferable to configure the staircase data adder 32 to perform the following processing on the first and second phase shift differential images $\psi_1(x, y)$ and $\psi_2(x, y)$.

Hereinafter, the first phase shift differential image $\psi_1(x,y)$ is described by way of example. First, the staircase data adder 32 scans one line in the Y direction from a corner (x=0, y=0), being the origin, of the first phase shift differential image $\psi_1(x, y)$, and boundary points at each of which the value changes from $\pi/2$ to $-\pi/2$ or from $-\pi/2$ to $\pi/2$ are detected. Upon crossing each of the boundary points from the origin, $\pi$ or $-\pi$ is added to the value. Thereby, an initial value $S_1(0, y)$ (x=0) is calculated. As shown in FIGS. 14A and 14B, when points $y_1$ and $y_2$ are detected, $S_1(0, y)$ is "0" when $0 \leq y < y_1$, "$-\pi$" when $y_1 \leq y < y_2$, "$-2\pi$" when $y_2 \leq y < y_3$, and "$-3\pi$" when $y_3 \leq y$.

Then, the staircase data adder 32 scans in the X direction from each of the y coordinates (x=0) to detect the boundary points. The value changes from $\pi/2$ to $-\pi/2$ or from $-\pi/2$ to $\pi/2$ when crossing each of the boundary points. The initial value $S_1(0, y)$ is added with $\pi$ or $-\pi$ when crossing each of the boundary points. Thereby, the first staircase data $S_1(x, y)$, which is changed by $\pi$ when crossing each boundary, is produced. The staircase data adder performs similar processing on the second phase shift differential image $\psi_2(x, y)$ to produce the second staircase data $S_2(x, y)$.

In the above description, the initial value $S_1(0, y)$ is obtained from the scanning in the Y direction from the origin. The first staircase data $S_1(x, y)$ is obtained from the scanning in the X direction from each of the y coordinates (x=0). Alternatively, the initial value $S_1(y, 0)$ is obtained from the scanning in the X direction from the origin. The first staircase data $S_1(x, y)$ is obtained from the scanning in the Y direction from each of the x coordinates (y=0). The value $S_1(0, 0)$ may be the value other than "0". Any of the four corners of the first phase shift differential image $\psi_1(x, y)$ may be used as the origin.

Second Embodiment

Figure 15:
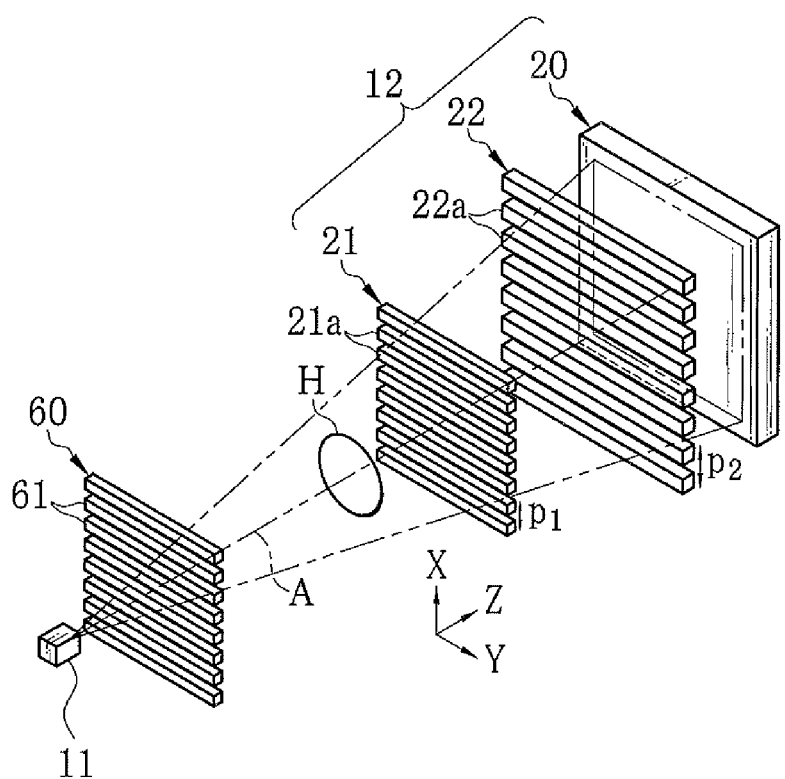
FIG. 15 is a multi-slit used in a second embodiment of the present invention.

In the first embodiment, when the distance between the X-ray source 11 and the FPD 20 is elongated, the image quality of the phase contrast image may be deteriorated by influence of blur in the G1 image due to the focal point size (generally in the order of 0.1 mm to 1 mm) of the X-ray focal point 11a. In a second embodiment of the present invention, as shown in FIG. 15, a multi-slit (source grating) 60 is disposed on the emission side of the X-ray source 11. The X-ray imaging system of the second embodiment is the same as that of the first embodiment except for the multi-slit 60.

The multi-slit 60 is an absorption-type grating having a configuration similar to those of the first and second absorption-type gratings 21 and 22. The multi-slit 60 has a plurality of X-ray shielding portions 61 extending in the Y direction and arranged periodically in the X direction. The multi-slit 60 partly blocks the X-rays from the X-ray source 11 to reduce the effective focal point size in the X direction. The multi-slit 60 forms a plurality of point light sources (dispersed light sources) in the X direction to reduce the blur in the G1 image. Note that, in a manner similar to the above, a low X-ray absorption portion (not shown) is provided between the X-ray shielding portions 61 adjacent in the X direction.

In this embodiment, even if there is a change in positions of gratings including the multi-slit 60 between the preliminary and main imaging, the artifact caused by the change is prevented.

Third Embodiment

In the first and second embodiments, the first absorption-type grating 21 is configured to linearly project the X-rays passed through the low X-ray absorption portions 21b. The present invention is not limited to this configuration. The first absorption-type grating 21 can be configured to diffract the X-rays so as to produce the so-called Talbot effect as disclosed in U.S. Pat. No. 7,180,979 corresponding to Japanese Patent No. 4445397. In a third embodiment of the present invention, the first absorption-type grating 21 is a diffraction grating and the distance $L_2$ between the first and second absorption-type gratings 21 and 22 is set to the Talbot length to constitute a Talbot interferometer. In this embodiment, the G1 image (self image) produced by the first grating 21 due to the Talbot effect is formed at the position of the second absorption-type grating 22.

In this embodiment, the first absorption-type grating 21 may be a phase-type grating (phase-type diffraction grating). In this case, the thickness and the material are determined such that a phase difference of "n" or "$\pi/2$" of the X-rays occurs between the high X-ray absorption portion 21a and the low X-ray absorption portion 21b.

Note that, in the first to third embodiments, the subject H is disposed between the X-ray source 11 and the first absorption-type grating 21. Alternatively, the subject H may be disposed between the first absorption-type grating 21 and the second absorption-type grating 22. Also in this configuration, the phase contrast image is produced in a manner similar to the above.

Fourth Embodiment

In the first to third embodiments, the second absorption-type grating 22 is provided separately from the FPD 20. The second absorption-type grating 22 can be omitted by the use of an X-ray image detector having a configuration disclosed in Japanese Patent Laid-Open Publication No. 2009-133823.

The X-ray image detector of this embodiment is a direct-conversion type X-ray image detector provided with a conversion layer for converting the X-rays into the charge and a charge collection electrode for collecting the charge converted in the conversion layer. The charge collection electrode of each pixel is composed of linear electrode groups each having linear electrodes. The linear electrodes are arranged at a predetermined period and electrically connected to each other. The linear electrode groups are arranged out of phase with each other. In this embodiment, the charge collection electrode constitutes the intensity modulator.

In FIG. 16, an FPD 70 of this embodiment has pixels 71 arranged at a predetermined pitch in two dimensions in the X and Y directions. Each of the pixels 71 is provided with a charge collection electrode 72 for collecting the charge converted by the conversion layer that converts the X-rays into the charge. The charge collection electrode 72 is composed of first to sixth linear electrode groups 72a to 72f. A phase of an arrangement period of the linear electrodes in each of the linear electrode groups is shifted by $\pi/3$. To be more specific, when the phase of the first linear electrode group 72a is 0, the phase of the second linear electrode group 72b is $\pi/3$; the phase of the third linear electrode group 72c is $2\pi/3$; the phase of the fourth linear electrode group 72d is $\pi$; the phase of the fifth linear electrode group 72e is $4\pi/3$; the phase of the sixth linear electrode group 72f is $5\pi/3$.

Each of the pixels 71 is provided with a switch group 73 for reading out the charge collected by the charge collection electrode 72. The switch group 73 is composed of a TFT switch provided to each of the first to sixth linear electrode groups 72a to 72f. The charge collected by each of the first to sixth linear electrode groups 72a to 72f is read out individually by controlling the switch group 73. Thereby, six types of G2 images out of phase with each other are detected by the single image capture. A phase contrast image is produced based on pieces of image data corresponding to the respective six types of G2 images. The configuration other than the above is the same as that in the first embodiment, so that description thereof is omitted.

In this embodiment, the second absorption-type grating 22 is unnecessary in the imaging unit 12. This reduces cost and enables further reduction in the thickness. In this embodiment, the G2 images provided with intensity modulation at different phases are detected in a single image capture. This makes physical scanning for the fringe scanning unnecessary and thus eliminates the use of the scan mechanism 23. Note that a charge collection electrode of another configuration disclosed in the Japanese Patent Laid-Open Publication 2009-133823 can be used instead of the charge collection electrode 72 of the above configuration.

In another embodiment which eliminates the use of the second absorption-type grating 22, the G1 image captured with the X-ray image detector is directly detected, and sampling is carried out periodically while the phase is changed by signal processing. Thereby, pieces of image data corresponding to G2 images out of phase with each other are produced.

Fifth Embodiment

In the first to fourth embodiments, the phase shift differential image is obtained using the fringe scanning method. Alternatively, the phase shift differential image may be obtained using Fourier transform method disclosed in WO2010/050483 corresponding to U.S. Pat. No. 8,009,797. In the Fourier transform method, a piece of image data obtained using the X-ray image detector is subjected to Fourier transform. Thereby, a Fourier spectrum of moiré fringes occurred in the image data is obtained. A spectrum corresponding to carrier frequency is separated from the Fourier spectrum, and inverse Fourier transform is performed. Thereby, the phase shift differential image is produced. In this case, there is no need to move the first and second absorption gratings 21 and 22, and thus the scan mechanism 23 is unnecessary.

Each of the above-described embodiments can be applied to radiation imaging systems for other uses including industrial use, in addition to the radiation imaging systems for medical diagnosing. Instead of the X-rays, gamma rays or the like can be used as the radiation.

Various changes and modifications are possible in the present invention and may be understood to be within the present invention.

What is claimed is:

1. A radiation imaging system comprising:
   a first grating for passing radiation from a radiation source to form a first periodic pattern image;
   an intensity modulator for providing intensity modulation to the first periodic pattern image to form at least one second periodic pattern image;
   a radiation image detector for detecting the second periodic pattern image to produce image data;
   a phase shift differential image generator for producing a phase shift differential image based on the image data;
   a staircase data generator for obtaining one or more boundaries, at each of which a value changes from $\pi/2$ to $-\pi/2$ or from $-\pi/2$ to $\pi/2$, in each of a first phase shift differential image, produced by the phase shift differential image generator in absence of a subject in preliminary imaging, and a second phase shift differential image, produced by the phase shift differential image generator in presence of the subject in main imaging, and producing first staircase data and second staircase data each changing by $\pi$ or $-\pi$ when crossing the boundary in a predetermined direction;
   a staircase data adder for adding the first staircase data to the first phase shift differential image to produce first added phase shift differential image and adding the second staircase data to the second phase shift differential image to produce second added phase shift differential image; and
   a subtraction processing section for subtracting the first added phase shift differential image from the second added phase shift differential image to produce a corrected phase shift differential image.

2. The radiation imaging system of claim 1, further comprising a phase contrast image generator for integrating the corrected phase shift differential image in a direction of a period of the first grating to produce a phase contrast image.

3. The radiation imaging system of claim 1, further comprising storage for storing the first added phase shift differential image.

4. The radiation imaging system of claim 3, further comprising:
   an input section for inputting an instruction for the preliminary imaging or the main imaging; and
   a controller for controlling the intensity modulator, the radiation image detector, the phase shift differential image generator, the staircase data generator, and the staircase data adder when the input section inputs the instruction for the preliminary imaging, and allowing the storage to store the first added phase shift differential image produced by the staircase data adder.

5. The radiation imaging system of claim 1, wherein the intensity modulator provides intensity modulation to the first periodic pattern image at relative positions out of phase with each other to produce the second periodic pattern images, and the radiation image detector detects the second periodic pattern images to produce the respective pieces of image data, and the phase shift differential image generator calculates a phase shift value of an intensity modulation signal, representing intensity changes in pixel data corresponding to the relative positions, based on the pieces of image data to produce the phase shift differential image.

6. The radiation imaging system of claim 5, wherein the intensity modulator is composed of a second grating and a scan mechanism, and a direction of a periodic pattern of the second grating is the same as that of the first periodic pattern image, and the scan mechanism moves one of the first and second gratings at a predetermined pitch.

7. The radiation imaging system of claim 6, wherein the first grating is an absorption-type grating and projects the radiation from the radiation source as the first periodic pattern image onto the second grating.

8. The radiation imaging system of claim 6, wherein the first grating is a phase-type grating and forms the radiation from the radiation source into the first periodic pattern image at a position of the second grating due to Talbot effect.

9. The radiation imaging system of claim 1, further comprising a source grating on an emission side of the radiation source.

10. An image processing method for a radiation imaging system, the radiation imaging system including a first grating for passing radiation from a radiation source to form a first periodic pattern image, an intensity modulator for providing intensity modulation to the first periodic pattern image to produce at least one second periodic pattern image, a radiation image detector for detecting the second periodic pattern image to produce image data, and a phase shift differential image generator for producing a phase shift differential image based on the image data, the image processing method comprising the steps of:

obtaining one or more boundaries, at each of which a value changes from $\pi/2$ to $-\pi/2$ or from $-\pi/2$ to $\pi/2$, in each of a first phase shift differential image, produced by the phase shift differential image generator in absence of a subject in preliminary imaging, and a second phase shift differential image, produced by the phase shift differential image generator in presence of the subject in main imaging, and producing first staircase data and second staircase data each changing by $\pi$ or $-\pi$ when crossing the boundary in a predetermined direction;

adding the first staircase data to the first phase shift differential image to produce a first added phase shift differential image and adding the second staircase data to the second phase shift differential image to produce a second added phase shift differential image; and subtracting the first added phase shift differential image from the second added phase shift differential image to produce a corrected phase shift differential image.

* * * * *